US006555335B1

(12) United States Patent
Saloheimo et al.

(10) Patent No.: US 6,555,335 B1
(45) Date of Patent: Apr. 29, 2003

(54) **XYLANASE FROM *TRICHODERMA REESEI*, METHOD FOR PRODUCTION THEREOF, AND METHODS EMPLOYING THIS ENZYME**

(75) Inventors: Markku La Saloheimo, Helsinki (FI); Matti Siika-Aho, Helsinki (FI); Maija Tenkanen, Espoo (FI); Merja E. Penttila, Helsinki (FI)

(73) Assignee: Genencor International, Inc., Palo Alto, CA (US)

( * ) Notice: Subject to any disclaimer, the term of this patent is extended or adjusted under 35 U.S.C. 154(b) by 0 days.

(21) Appl. No.: 09/658,772

(22) Filed: Sep. 11, 2000

Related U.S. Application Data

(60) Provisional application No. 60/173,889, filed on Dec. 30, 1999.

(51) Int. Cl.$^7$ ............................. C12P 1/00; C12N 15/74; C12N 9/00; C12N 9/14; C12N 1/21

(52) U.S. Cl. ......................... 435/41; 435/471; 435/183; 435/195; 435/252.31; 435/252.33; 435/254.6

(58) Field of Search ................................. 435/183, 200, 435/209, 220, 223, 225, 195, 471, 252.31, 253.33, 254.6, 41

(56) References Cited

U.S. PATENT DOCUMENTS

| | | | |
|---|---|---|---|
| 4,816,567 A | 3/1989 | Cabilly et al. | 530/387.3 |
| 5,010,182 A | 4/1991 | Brake et al. | 536/23.7 |
| 5,405,769 A | 4/1995 | Campbell et al. | 435/200 |
| 5,437,999 A | 8/1995 | Diebold et al. | 204/403.11 |
| 5,866,408 A | 2/1999 | Sung et al. | 435/278 |
| 5,922,579 A | 7/1999 | Fagerstrom et al. | 435/99 |

FOREIGN PATENT DOCUMENTS

| | | |
|---|---|---|
| EP | 0 036 776 | 5/1988 |
| EP | 0 362 179 | 4/1990 |
| EP | 0 073 657 | 12/1990 |
| WO | WO 89/05859 | 6/1989 |
| WO | WO 90/13646 | 11/1990 |

OTHER PUBLICATIONS

Altschul, Stephen F. et al., "Local Alignment Statistics," *Methods in Enzymology,* vol. 266, pp. 460–480, 1996.
Altschul, Stephen F. et al., "Basic Local Alignment Search Tool," *J. Mol. Biol.,* vol. 215, pp. 403–408, 1990.
Ausubel, Frederick M. et al., ed. *Current Protocols in Molecular Biology,* John Wiley & Sons, Inc., Ch. 9, 1995.
Bennett, J.W. et al., "More Gene Manipulations in Fungi," Academic Press, San Diego, pp. 70–76, 1991.
Berges, Thierry et al., "Isolation of uridine auxotrophs from *Trichoderma reesei* and efficient transformation with the cloned ura3 and ura5 genes," *Curr. Genet.* vol. 19, pp. 359–365, 1991.

Biely, P. et al., "Endo–β–1,4–xylanase families: differences in catalytic properties," *Journal of Biotechnology,* vol. 57, pp. 151–166, 1997.
Brodeur, Bernard R. et al., "Mouse–Human Myeloma Partners for the Production of Heterohybridomas," *Monoclonal Antibody Production Techniques and Applications,* Lawrence B. Schook, ed., Marcel Dekker, Inc., New York, pp. 51–63, 1987.
Carter, Paul et al., "Improved oligonucleotide site–directed mutagenesis using M13 vectors," *Nucleic Acids Research,* vol. 13, No. 12, pp. 4431–4443, 1985.
Chang, Annie C. Y. et al., "Phenotypic expression in *E. coli* of a DNA sequence coding for mouse dihydrofolate reductase," *Nature,* vol. 275, pp. 617–624, Oct. 19, 1978.
Chothia, Cyrus, "The Nature of the Accessible and Buried Surfaces in Proteins," *J. Mol. Biol.,* vol. 105, pp. 1–14, 1976.
De Boer, Herman A. et al., "The tac promoter: A functional hybrid derived from the trp and lac promoters," *Proc. Natl. Acad. Sci., U.S.A.,* vol. 80, pp. 21–25, Jan., 1983.
Deutscher, Murray P., "Rethinking Your Purification Procedure," *Methods in Enzymology,* vol. 182, No. 57, pp. 779, 1990.
Georis, Jacques et al., "An additional aromatic interaction improves the thermostability and thermophilicity of a mesophilic family 11 xylanase: Structural basis and molecular study," *Protein Science,* Cambridge University Press, vol. 9, pp. 466–475, 2000.
Goding, James W. "Production and Application of Monoclonal Antibodies in Cell Biology, Biochemistry and Immunology," *Monoclonal Antibodies: Principles and Practice,* Academic Press, pp. 59–103, 1986.
Goeddel, David V. et al., "Direct expression in *Escherichia coli* of a DNA sequence coding for human growth hormone," *Nature,* vol. 281, pp. 544–548, Oct. 18, 1979.
Goeddel, David V. et al., "Synthesis of human fibroblast interferon by *E. coli,*" *Nucleic Acids Research,* vol. 8, No. 18, pp. 4057–4–74, 1980.
Henrissat, Bernard, "Analysis of hemicellulases sequences. Relationships to other glycanases," *Xylans and Xylanases,* ed. by J. Visser et al., Elsevier Science Publishers, pp. 97–110, 1992.
Hess, B. et al., "Cooperation of Glycolytic Enzymes," *Advances in Enzyme Regulation,* vol. 7, pp. 149–167, Pergamon Press, 1968.

(List continued on next page.)

*Primary Examiner*—Remy Yucel
*Assistant Examiner*—Katherine F Davis
(74) *Attorney, Agent, or Firm*—Genencor International, Inc

(57) ABSTRACT

The present invention is directed to novel xylanases (referred to as XYL-IV) and to nucleic acid molecules encoding those xylanases. Also provided herein are vectors and host cells including those nucleic acid sequences, antibodies which bind to the xylanases of the present invention, methods for producing the xylanases of the present invention, and methods employing the xylanases of the present invention.

10 Claims, 7 Drawing Sheets

OTHER PUBLICATIONS

Hitzeman, Ronald A. et al., "Isolation and Characterization of the Yeast 3–Phosphoglycerokinase Gene (PGK) by an Immunological Screening Technique," *The Journal of Biological Chemistry*, vol. 255, No. 24, pp. 12073–12080, Dec. 25, 1980.

Holland, Michael J. et al., "Isolation and Identification of Yeast Messenger Ribonucleic Acids Coding for Enolase, Glyceraldehyde–3–phosphate Dehydrogenase, and Phosphoglycerate Kinase," *Biochemistry*, vol. 17, No. 23, pp. 4900–4907, 1978.

Hsiao, Chu–Lai et al., "High–frequency transformation of yeast by plasmids containing the cloned yeast ARG4 gene," *Proc. Natl. Acad. Sci. USA*, vol. 76, No. 8, pp. 3829–3853, Aug., 1979.

Jones, Elizabeth W., "Proteinase Mutants of *Saccharomyces Cerevisiae*," *Genetics*, vol. 85, pp. 23–33, Jan., 1977.

Kingsman, Alan J. et al., "Replication in *Saccharomyces cerevisiae* of Plasmid pBR313 Carrying DNA from the Yeast trpl Region," *Gene*, vol. 7, pp. 141–152, 1979.

Kohler et al., "Continuous cultures of fused cells secreting antibody of predefined specificity," *Nature*, vol. 256, pp. 495–499, Aug. 7, 1975.

Kozbor, Danuta et al., "A Human Hybrid Myeloma for Production of Human Monoclonal Antibodies," *The Journal of Immunology*, vol. 133, No. 6, pp. 3001–3005, Dec. 1984.

Kubata, Bruno Kilunga et al., "Xylanase IV, an Exoxylanase of Aeromonas caviae ME–1 Which Produced Xylotetraose as the Only Low–Molecular–Weight Oligosaccharide from Xylan," *App. Env. Microb.*, vol. 61, No. 4, pp. 1666–1668, Apr., 1995.

McPherson, Michael J. et al, "PCR with highly degenerate primers," *PCR A Practical Approach*, pp. 171–186, 1991.

Merrifield, R.B., "Solid Phase Peptide Synthesis. I. The Synthesis of a Tetrapeptide," *J. Am. Chem. Soc.* vol. 85, pp. 2149–2154, 1963.

Munson, Peter et al., "Ligand: A Versatile Computerized Approach for Characterization of Ligand–Binding Systems," Analytical Biochemistry, vol. 107, pp. 220–239, 1980.

Needleman, Saui B. et al., "A General Method Applicable to the Search for Similarities in the Amino Acid Sequence of Two Proteins," *J. Mol. Biol.*, vol. 48, pp. 443–453, 1970.

Pearson, William R. et al., "Improved tools for biological sequence comparison," *Proc. Natl. Acad. Sci. USA*, vol. 85, pp. 2444–2448, Apr., 1988.

Sambrook, J. et al., *Molecular Cloning: A Laboratory Manual*, Cold Spring Harbor Laboratory Press, 1989.

Shaw, Charles H. et al., "A General Method for the Transfer of Cloned Genes to Plant Cells," Gene, vol. 23, pp. 315–330, 1983.

Sheir–Neiss, G. et al., "Characterization of the secreted cellulases of *Trichoderma reesei* wild type and mutants during controlled fermentations," *Appl. Microbiol. Biotechnol.*, vol. 20, pp. 46–53, 1984.

Silva, Claudio et al., "Evaluation of hydrolysis products of xylans by xylan–degrading enzymes from *Humicola grisea* var. *thermoidea* and *Aspergillus fumigatus* Fresenius," *World Journal of Microbiology & Biotechnology*, vol. 16, pp. 81–83, 2000.

Smith, Temple F. et al., "Comparison of Biosequences," *Advances in Applied Mathematics*, vol. 2, pp. 482–489, 1981.

Stinchcomb, D.T. et al., "Isolation and characterisation of a yeast chromosomal replicator," *Nature*, vol. 282, pp. 39–43, Nov. 1, 1979.

Suorninen Pirkko et al., ed., "*Trichoderma Reesei* Cellulases and Other Hydrolases," Proceedings of The TRICEL93 Symposium, pp. 125–135, Jun. 2–5, 1993, Espoo, Finland.

Thomas, Patricia S. "Hybridization of denatured RNA and small DNA fragments transferred to nitrocellulose," *Proc. Natl. Acad. Sci. USA*, vol. 77, No. 9, pp. 5201–5205, Sep., 1980.

Tschumper, Gary et al., "Sequence of a yeast DNA fragment containing a chromosomal replicator and the TRP1 gene," *Gene*, vol. 10, pp. 157–166, 1980.

van Solingen, Pieter et al., "Fusion of Yeast Spheroplasts," Journal of Bacteriology, vol. 130, No. 2, pp. 946–947, May, 1977.

Ward, Michael et al., "Use of Aspergillus overproducing mutants, cured for integrated plasmid, to overproduce heterologous proteins," Appl. Microbiol. Biotechnol., vol. 39, pp. 738–743, 1993.

Wakarchuk, Warren, W. et al., "Thermostabilization of the *Bacillus circulans* xylanase by the introduction of disulfide bonds," *Protein Engineering*, vol. 7, No. 11, pp. 1379–1386, 1994.

Wells, J.A. et al., "Importance of hydrogen–bond formation in stabilizing the transition state of subtilisin," Phil. Trans. R. Soc. Lond., vol. 317, pp. 415–423, 1986.

Zoller, Mark J. et al., "Oligonucleotide–directed mutagenesis using M13–derived vectors: an efficient and general procedure for the production of point mutations in any fragment of DNA," Nucleic Acids Research, vol. 10, No. 20, pp. 6487–6500, 1982.

Copy of International Search Report for PCT/US00/24747.

Xu, J., et al., "A third xylanase from *Trichoderma reesei* PC 3–7," Applied Microbiology and Biotechnology, (1998) vol. 49, No. 6, pp. 718–724 (XP000990807).

Kershaw, J., "Amycolatopsis orientalis cosmid PCZA361," Database EMBL Online! Accession AJ223998 (1998) (XP002164289)

Okai, N., et al., "Endo–Xylanase," Database Swissprot Online! Accession P70733 (1997) (XP002164290).

FIG._1

```
CTTCTCTCTACTTTCTCCTCGACATGAAGTCATCTATCTCTGTTGTTTGGCTCTTCTCGGCCATAGCGCTG
CATGGTCATACGCCACCAAGTCTCAATACAGGCTAACATCAAGATCAATGCCCGCCAGACCTATCAGACGA
TGATTGGAGGGGTGTTCGGCGCCTTTGTATTGCTTGTCGCAATTGGGTCTTCTGGTCTGTCGCCTG
AGAACCAACAGAAGGTTACCCAGATTCTCTTCGATGAGAACATTGGCGGCCTGTCTATTGTTCGAATGATA
TCGGCTCCTCGCCAGGAACCACCATTTGCCAACCTGTCCCCGACGCCCAAGACAAGTTCGACTATGTGT
GGGATGGCAGTGACAACTGCCAGTTTAACCTCCAAAACAGCTCTCAAATACAATCGAACCTTTACGTTT
ACGCGGATGCCTGGTCCGTCCCGCTGCATGAAGACGGTCGGGACTGAGAACCTCGGAGGCAAATCTGCG
GTGTGCGAGGAACCGATTGCAAACACGATCGATATCTCCCTCTAGGCGCCCAAGCATATGCCGATTACTCGTACAATATGTCCGCT
TCTATAAAGAGAAGGCATGCTTTCGACGCATGATATCTCCCTCTAGGCGCCCAAGCATATGCCGATTACTCGTACAATATGTCCGCT
ACGAGAGCATGCTTTCGACGCATCAGCTCAGCTGCGATGCAACTGGCGCCCAAGAGAGAAACATTCTTATGAGC
CTTTCCCGAAAGTAGACGTCAGCTCAGCTGCGATGCAACTGGCGCCCAAGAGAGAAACATTCTTATGAGC
TCCAGCGGGTGGCGAGAGATACTTTGACATTGCGACATGGCACACATACCAAAGCAACCAGAGCGCC
CATTCAACGCCGGTGGAAAGCCAAACATACAGACTGAGTGGGCAGATGGGCATTATATGCACAACGCGTTGTCAACAGCG
GGATTATAGCGGCCAACTTGCTGAGGGCCTCCAATGGGCATTATATGCACAACGCGTTGTCAACAGCG
ACACCTCAGGCTACACGCCACTGGTGGTGCACAGAACACCAACGGCGACAACGCCCTCATCCGCCTTGATC
GCGACAGCTACGAGGTGTCGGCTGCGAGAACGTCGAGAACGTCTATGTGACCGCATATGTCAACAAGAATGAACCGTTG
TCCGCATTGGTGCAACAAGCGACGTCGAGAACGTCTATGTGACCGCATATGTCAACAAGAATGAACCGTTG
CTATTCCCGTCATCAACGCCGCTCACTTCCTTACGACCTTACAATGCATCGATCTGAGGGTATCAAGAGAGGA
AGCTGAGCGAGTACTTGACGGACAATAGCCACAACGTCACCTTGCAAGTCGGTACAAGGTCTCTGTAGCA
GTCTGAAGGTGACTGTTGAGCCGAGAGCGATGAAGACTTTTGGTTGGAGTAAGAACTCGTACGGACGATG
GAAGTGTCGTGACCGTGTATACTTTTTCACATAGCCGCAATCGACGTTTGCCGTCATCGACGAGGGAA
AAAAAA
```

FIG._2

```
MKSSISVVLALLGHSAAWSYATKSQYRANIKINARQTYQTMIGGCSGAFGIACQQFGSSGLSPENQQKV
TQILFDENIGGLSIVRNDIGSSPGTTILPTCPATPQDKFDYVWDGSDNCQFNLTKTALKYNPNLYVYADA
WSAPGCMKTVGTENLGGQICGVRGTDCKHDWRQAYADYLVQYVRFYKEEGIDISLLGAWNEPDFNPFTYE
SMLSDGYQAKDFLEVLYPTLKKAFPKVDVSCCDATGARQERNILYELQQAGGERYFDIATWHNYQSNPER
PFNAGGKPNIQTEWADGTGPWNSTWDYSGQLAEGLQWALYMHNAFVNSDTSGYTHWCAQNTNGDNALIR
LDRDSYEVSARLWAFAQYFRFARPGSVRIGATSDVENVYVTAYVNKNGTVAIPVINAAHFPYDLTIDLEG
IKKRKLSEYLTDNSHNVTLQSRYKVSGSSLKVTVEPRAMKTFWLE
```

FIG._3a

```
        BseRI          EclHKI                              EarI
        .....          .....                               SapI
                                                           .....
CTTCTCTACTTTCTCCTCTGACATGAAGTCATCTATCTCTGTGTTTTGGCTCTTCTGGGGCTCATAGCGCTGCATGGTCATACGCCACCA    90
                M  K  S  S  I  S  V  V  L  A  L  L  G  H  S  A  A  V  S  Y  A  T

KasI
                                                                            .....
AGTCTCAATACAGGGCTAACATCAAGATCAATGCCCGCAGACCTATCAGAGACGATGATTGGAGGGGGTTGTTCGGGGCGCCTTTGGTATTG   180
 K  S  Q  Y  R  A  N  I  K  I  N  A  R  Q  T  Y  Q  T  M  I  G  G  C  S  G  A  F  G  I
                        BbsI                    BstEII                    EarI
                        .....                   .....                     .....
CTTGTCAGCAATTCGGGTCTTCTTTCTGGTCTGTGTCGCCTGAGAATCAACAGAAGGTTACCCAGATTCTCTTCGATGAGAACATTGGGGCCTGT   270
 A  C  Q  Q  F  G  S  S  G  L  S  P  E  N  Q  Q  K  V  T  Q  I  L  F  D  E  N  I  G  G  L
        BseRI                                                                         RleAI
        .....                                                                         .....
CTATTGTTCGGAATGATATCGGCTCCTCCTCGCCCAGGAACCACCATTTTGCCAACCTGTCCCGACGCCGCAAGACAAGTTCGACTATGTGT    360
 S  I  V  R  N  D  I  G  S  S  P  G  T  T  I  L  P  T  C  P  A  T  P  Q  D  K  F  D  Y  V
                                                                                      BsrBI
                                                                                      .....
GGGATGGCAGTGACAACTGCCAGTTTAACCTCACCAAAACAGCTCTCAAATACAATCCGAACCTTTACGGCGTTTACGGCGGATGCCTGGTCCG   450
 W  D  G  S  D  N  C  Q  F  N  L  T  K  T  A  L  K  Y  N  P  N  L  Y  V  V  Y  A  D  A  W  S
        BbsI                                                                         KasI
        .....                                                                        .....
CTCCCGGCTGCATGAAGACGGTCGGGACTGAGAACCTCGGAGGGCAAATCTGCGGTGTGCGAGGAACCGATTGCAAACACGACTGGCGCC      540
 A  P  G  C  M  K  T  V  G  T  E  N  L  G  G  Q  I  C  G  V  R  G  T  D  C  K  H  D  W  R
```

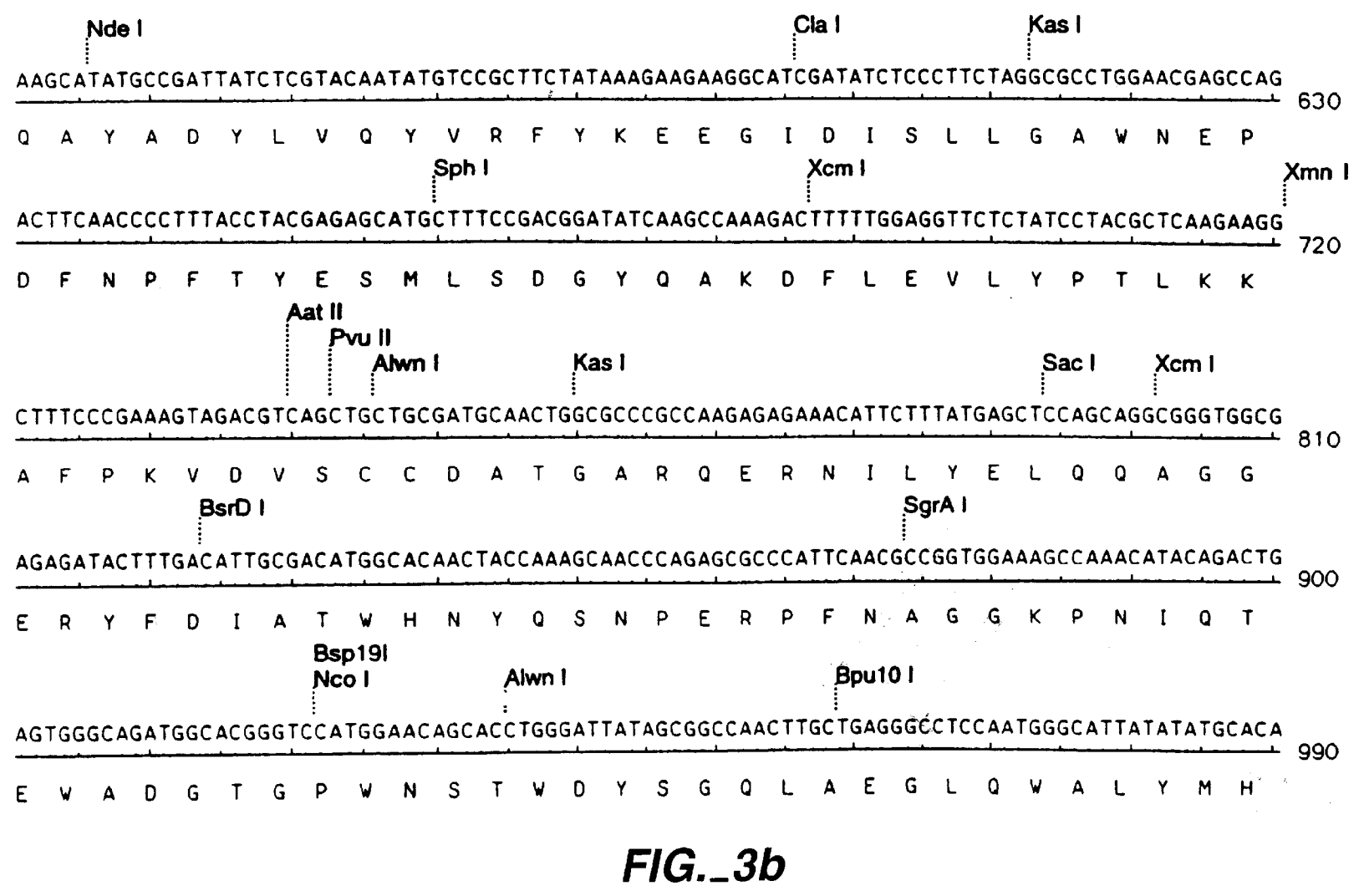

FIG._3b

```
Mlu I                Bsu36 I                   ApaL I
ACGCGTTTGTCAACAGGACCACCTCAGGCTACACGCACTGGTGTGCACAGAACACCAACGGCGACAACGCCCTCATCCGCCTTGATC   1080
 N  A  F  V  N  S  D  T  S  G  Y  T  H  W  V  C  A  Q  N  T  N  G  D  N  A  L  I  R  L  D
Nru I
                                                                                BsrB I
GCGACAGCTACGAGGTGTCGGCGCTCGCCTTTGCCCAATACTTCCGCTTTGCCCGGCCCGGATCTGTCCGCATTGGTGCAACAA     1170
 R  D  S  Y  E  V  S  A  R  L  W  A  F  A  Q  Y  F  R  F  A  R  P  G  S  V  R  I  G  A  T
        Aat II              Nde I

Sca I
GCGACGTCGAGAACGTCTATGTGACCGCATATGTCAACAAGAATGGAACCGTTGCTATTCCCGTCATCAACGCCGCTCACTTTCCTTACG 1260
 S  D  V  E  N  V  Y  V  T  A  Y  V  N  K  N  G  T  V  A  I  P  V  I  N  A  A  H  F  P  Y
        Cla I                       Ear I

Bbs I        BsiW I
ACCTTACAATCGATCTGGAGGGTATCAAGAAGAGAGGAAGCTGAGCGAGTACTTGACGGACAATAGCCACAACGTCACCTTGCAAAGTCGGT 1350
 D  L  T  I  D  L  E  G  I  K  K  R  K  L  S  E  Y  L  T  D  N  S  H  N  V  T  L  Q  S  R
   Bsa I

Nde I
ACAAGGTGTCTGGTAGCAGTCTGAAGGTGACTGTTGAGCCGAGAGCGATGAAGACTTTTGGTTGGAGTAAGAACTCGTACGGGACGATG    1440
 Y  K  V  S  G  S  S  L  K  V  T  V  E  P  R  A  M  K  T  F  W  L  E
        Bst1107 I

GGAAGTGTCGTGACCAGTGTATACTTTTTTCACATATGAGCAGGAAAAAAA                                          1518
```

FIG._3C

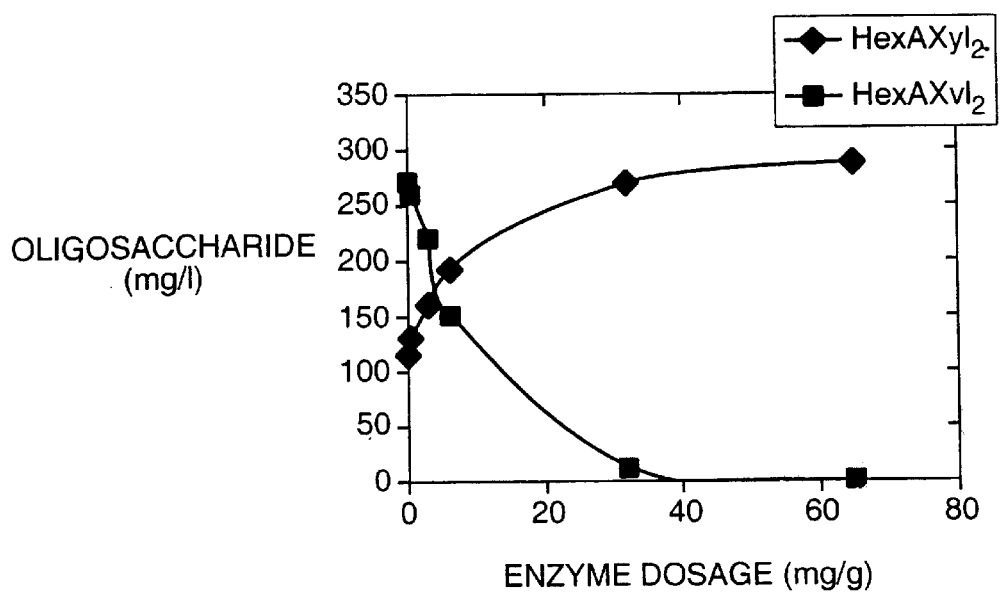
FIG._4
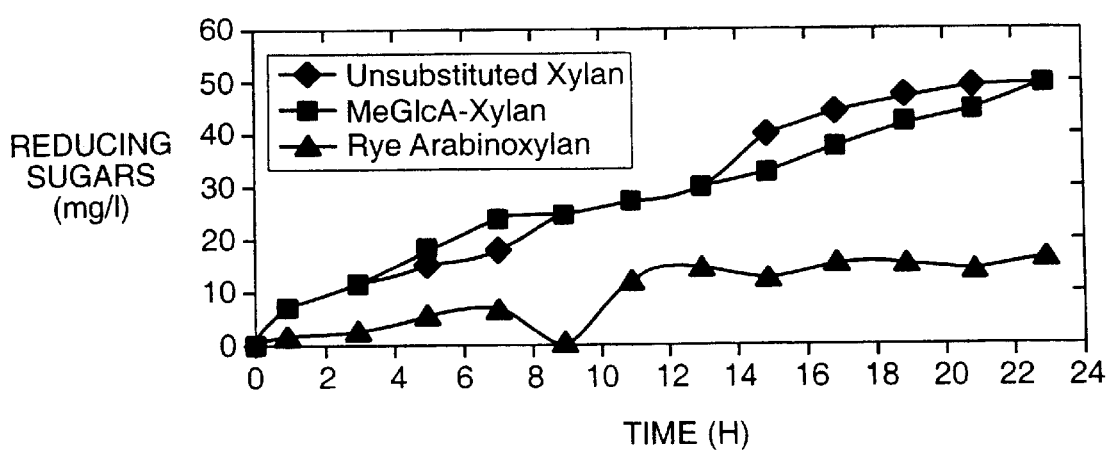
FIG._5

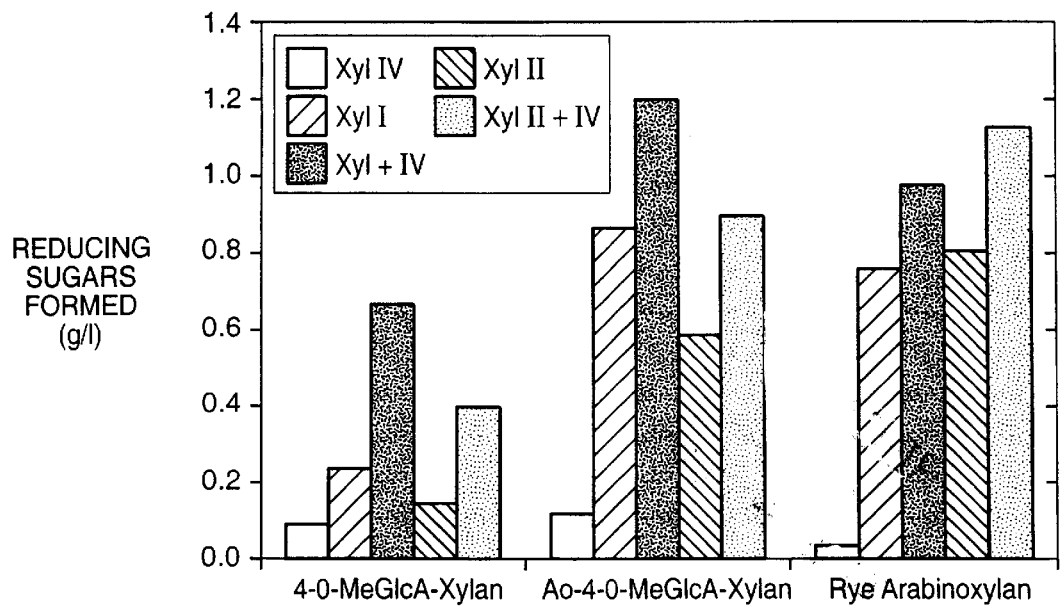
FIG._6a
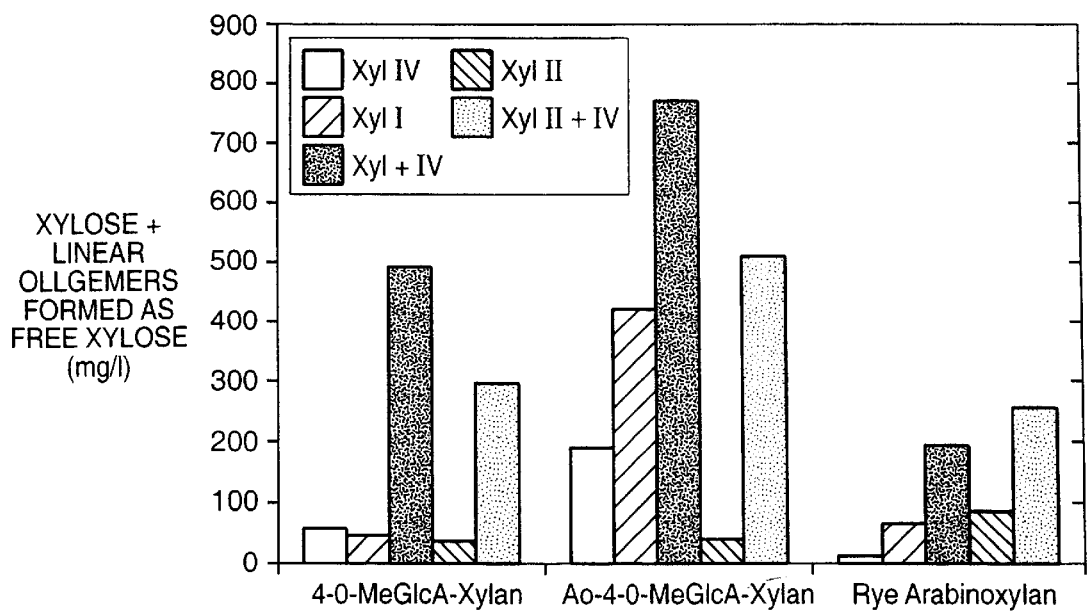
FIG._6b

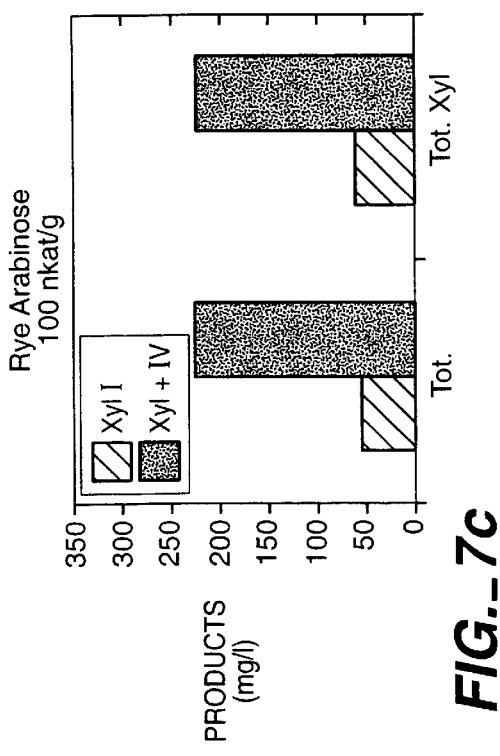
FIG._7a
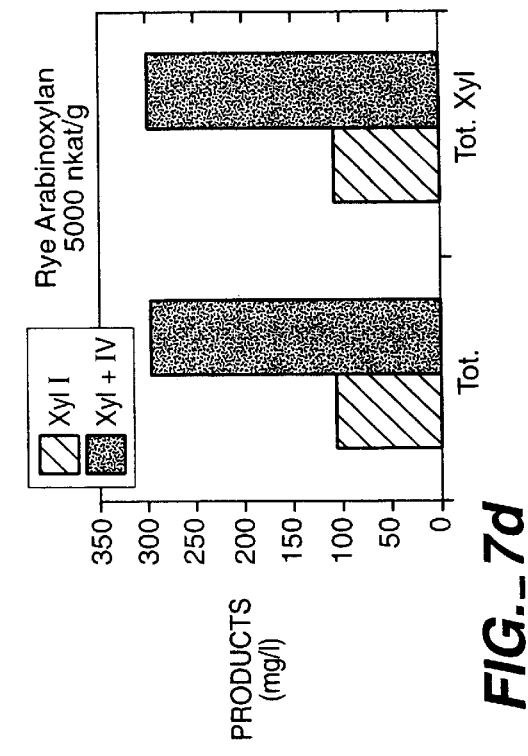
FIG._7b
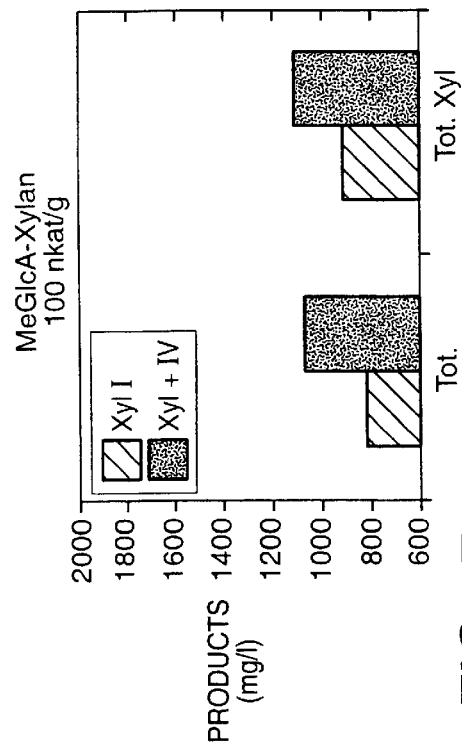
FIG._7c
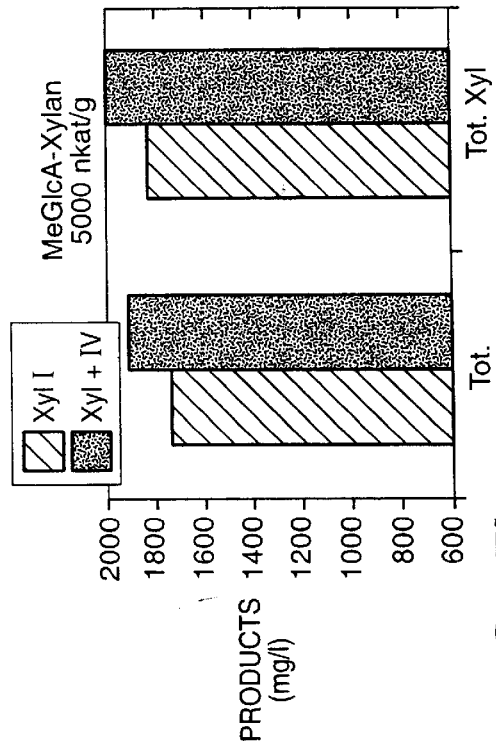
FIG._7d

SEQUENCE LISTING

```
<160> NUMBER OF SEQ ID NOS: 3

<210> SEQ ID NO 1
<211> LENGTH: 1518
<212> TYPE: DNA
<213> ORGANISM: Artificial Sequence
<220> FEATURE:
<223> OTHER INFORMATION: cDNA clone from Trichoderma reesei RNA

<400> SEQUENCE: 1
cttctctcta ctttctcctc gacatgaagt catctatctc tgttgttttg gctcttctgg      60
gccatagcgc tgcatggtca tacgccacca agtctcaata cagggctaac atcaagatca     120
atgcccgcca gacctatcag acgatgattg gaggggttg ttcgggcgcc tttggtattg      180
cttgtcagca attcgggtct tctggtctgt cgcctgagaa ccaacagaag gttacccaga     240
ttctcttcga tgagaacatt ggcggcctgt ctattgttcg gaatgatatc ggctcctcgc     300
caggaaccac cattttgcca acctgtcccg cgacgccgca agacaagttc gactatgtgt     360
gggatggcag tgacaactgc cagtttaacc tcaccaaaac agctctcaaa tacaatccga     420 accttttacgt ttacgcggat gcctggtccg ctcccggctg catgaagacg gtcgggactg     480
agaacctcgg agggcaaatc tgcggtgtgc gaggaaccga ttgcaaacac gactggcgcc     540
aagcatatgc cgattatctc gtacaatatg tccgcttcta taaagaagaa ggcatcgata     600
tctcccttct aggcgcctgg aacgagccag acttcaaccc ctttacctac gagagcatgc     660
tttccgacgg atatcaagcc aaagacttt tggaggttct ctatcctacg ctcaagaagg      720
ctttcccgaa agtagacgtc agctgctgcg atgcaactgg cgcccgccaa gagagaaaca     780
ttctttatga gctccagcag gcgggtggcg agagatactt tgacattgcg acatggcaca     840
actaccaaag caacccagag cgcccattca acgccggtgg aaagccaaac atacagactg     900
agtgggcaga tggcacgggt ccatggaaca gcacctggga ttatagcggc caacttgctg     960
agggcctcca atgggcatta tatatgcaca acgcgttgt caacagcgac acctcaggct    1020
acacgcactg gtggtgtgca cagaacacca acggcgacaa cgccctcatc cgccttgatc    1080
```

-continued

```
gcgacagcta cgaggtgtcg gctcgccttt gggcttttgc ccaatacttc cgctttgccc      1140
ggcccggatc tgtccgcatt ggtgcaacaa gcgacgtcga gaacgtctat gtgaccgcat      1200
atgtcaacaa gaatggaacc gttgctattc ccgtcatcaa cgccgctcac tttccttacg      1260
accttacaat cgatctggag ggtatcaaga gaggaagct gagcgagtac ttgacggaca       1320
atagccacac cgtcaccttg caaagtcggt acaaggtctc tggtagcagt ctgaaggtga      1380
ctgttgagcc gagagcgatg aagactttt ggttggagta agaactcgta cgggacgatg      1440
ggaagtgtcg tgaccgtgta tacttttttc acataggccg caatcgacgt ttgccgtcat     1500
atgagcaggg aaaaaaaa                                                   1518
```

<210> SEQ ID NO 2
<211> LENGTH: 465
<212> TYPE: PRT
<213> ORGANISM: Trichoderma reesei

<400> SEQUENCE: 2

```
Met Lys Ser Ser Ile Ser Val Val Leu Ala Leu Leu Gly His Ser Ala
  1               5                  10                  15

Ala Trp Ser Tyr Ala Thr Lys Ser Gln Tyr Arg Ala Asn Ile Lys Ile
             20                  25                  30

Asn Ala Arg Gln Thr Tyr Gln Thr Met Ile Gly Gly Cys Ser Gly
         35                  40                  45

Ala Phe Gly Ile Ala Cys Gln Gln Phe Gly Ser Ser Gly Leu Ser Pro
     50                  55                  60

Glu Asn Gln Gln Lys Val Thr Gln Ile Leu Phe Asp Glu Asn Ile Gly
 65                  70                  75                  80

Gly Leu Ser Ile Val Arg Asn Asp Ile Gly Ser Ser Pro Gly Thr Thr
                 85                  90                  95

Ile Leu Pro Thr Cys Pro Ala Thr Pro Gln Asp Lys Phe Asp Tyr Val
            100                 105                 110

Trp Asp Gly Ser Asp Asn Cys Gln Phe Asn Leu Thr Lys Thr Ala Leu
        115                 120                 125

Lys Tyr Asn Pro Asn Leu Tyr Val Tyr Ala Asp Ala Trp Ser Ala Pro
    130                 135                 140

Gly Cys Met Lys Thr Val Gly Thr Glu Asn Leu Gly Gly Gln Ile Cys
145                 150                 155                 160

Gly Val Arg Gly Thr Asp Cys Lys His Asp Trp Arg Gln Ala Tyr Ala
                165                 170                 175

Asp Tyr Leu Val Gln Tyr Val Arg Phe Tyr Lys Glu Gly Ile Asp
            180                 185                 190

Ile Ser Leu Leu Gly Ala Trp Asn Glu Pro Asp Phe Asn Pro Phe Thr
        195                 200                 205

Tyr Glu Ser Met Leu Ser Asp Gly Tyr Gln Ala Lys Asp Phe Leu Glu
    210                 215                 220

Val Leu Tyr Pro Thr Leu Lys Lys Ala Phe Pro Lys Val Asp Val Ser
225                 230                 235                 240

Cys Cys Asp Ala Thr Gly Ala Arg Gln Glu Arg Asn Ile Leu Tyr Glu
                245                 250                 255

Leu Gln Gln Ala Gly Gly Glu Arg Tyr Phe Asp Ile Ala Thr Trp His
            260                 265                 270

Asn Tyr Gln Ser Asn Pro Glu Arg Pro Phe Asn Ala Gly Gly Lys Pro
        275                 280                 285

Asn Ile Gln Thr Glu Trp Ala Asp Gly Thr Gly Pro Trp Asn Ser Thr
```

```
                    290                 295                 300
Trp Asp Tyr Ser Gly Gln Leu Ala Glu Gly Leu Gln Trp Ala Leu Tyr
305                 310                 315                 320

Met His Asn Ala Phe Val Asn Ser Asp Thr Ser Gly Tyr Thr His Trp
                325                 330                 335

Trp Cys Ala Gln Asn Thr Asn Gly Asp Asn Ala Leu Ile Arg Leu Asp
                340                 345                 350

Arg Asp Ser Tyr Glu Val Ser Ala Arg Leu Trp Ala Phe Ala Gln Tyr
            355                 360                 365

Phe Arg Phe Ala Arg Pro Gly Ser Val Arg Ile Gly Ala Thr Ser Asp
    370                 375                 380

Val Glu Asn Val Tyr Val Thr Ala Tyr Val Asn Lys Asn Gly Thr Val
385                 390                 395                 400

Ala Ile Pro Val Ile Asn Ala Ala His Phe Pro Tyr Asp Leu Thr Ile
                405                 410                 415

Asp Leu Glu Gly Ile Lys Lys Arg Lys Leu Ser Glu Tyr Leu Thr Asp
                420                 425                 430

Asn Ser His Asn Val Thr Leu Gln Ser Arg Tyr Lys Val Ser Gly Ser
            435                 440                 445

Ser Leu Lys Val Thr Val Glu Pro Arg Ala Met Lys Thr Phe Trp Leu
    450                 455                 460

Glu
465

<210> SEQ ID NO 3
<211> LENGTH: 15
<212> TYPE: PRT
<213> ORGANISM: Artificial Sequence
<220> FEATURE:
<223> OTHER INFORMATION: an N-terminal amino acid sequence of the mature
      XYL-IV
<221> NAME/KEY: VARIANT
<222> LOCATION: (1)...(15)
<223> OTHER INFORMATION: Xaa = Any Amino Acid

<400> SEQUENCE: 3

Xaa Ser Tyr Ala Thr Xaa Ser Gln Tyr Xaa Ala Asn Ile Xaa Ile
1               5                   10                  15
```

XYLANASE FROM *TRICHODERMA REESEI*, METHOD FOR PRODUCTION THEREOF, AND METHODS EMPLOYING THIS ENZYME

CROSS REFERENCE TO RELATED APPLICATIONS

This Application claims priority to U.S. Ser. No. 60/173,889, filed Dec. 30, 1999.

GOVERNMENT SPONSORED RESEARCH AND DEVELOPMENT

Not Applicable.

BACKGROUND OF THE INVENTION

The complex structure of wood includes cellulose, hemicellulose and lignin, along with other minor components. Lignin is associated with cellulose and hemicellulose, and is probably partially covalently bound to both cellulose and hemicellulose. In the paper-making process, lignin is generally removed from the wood pulp since it lends a brownish color, reduces strength and imparts other undesirable characteristics to the finished product. Removal of lignin can be achieved in many ways.

A majority of the lignin is initially removed from wood pulp through chemical pulping (e.g., the Kraft process). In the subsequent bleaching process, chemical pulp is routinely reacted with chlorine and other delignifying chemicals to further remove lignin and then reacted with bleaching agents to modify the lignin from pulp, providing a stable brightened pulp. However, the treatment with chlorine is undesirable from an environmental standpoint because the resulting effluents contain a large number of toxic compounds (e.g,. chlorinated phenolics). Concern about the environmental harmful effects caused by pulp bleaching with chlorine containing chemicals has driven the industry to seek alternative bleaching methods.

Attempts to use xylanases and other enzymes derived from fungal and bacterial sources to enhance delignification and brightening, while lowering or eliminating the use of chlorine chemicals, have been described in the literature. However, existing enzyme systems generally do not readily achieve degradation of hemicellulose or delignification to a sufficient extent. The extent of hemicellulose degradation and delignification could be improved by employing additional xylanases that cleave xylan in a different manner or that act synergistically with other xylanases, hemicellulases, other enzymes, or even chemicals.

Numerous xylanases from fungal and bacterial microorganisms have been identified and characterized. (See, e.g., U.S. Pat. No. 5,437,992; Coughlin, M. P. supra; Biely, P. et al., *Proceedings of the second TRICEL symposium on Trichoderma reesei Cellulases and Other Hydrolases*, Espoo 1993, P. Souminen and T. Reinikainen eds., Foundation for Biotechnical and Industrial Fermentation Research 8:125–135 (1993)). In particular, three specific xylanases (XYL-I, XYL-II, and XYL-III) have been identified in *T. reesei* (Tenkanen, et al., *Enzyme Microb. Technol.* 14:566 (1992); Törrönen, et al., *Bio/Technology* 10:1461 (1992); and Xu, et al., *Appl. Microbiol. Biotechnol.* 49:718 (1998)).

Although numerous xylanases have been described in the literature, the need still exists to identify novel xylanases that are more effective in applications relating to animal feed, grain processing, biofuels, cleaning, fabric care, chemicals, plant processing, and delignifying and brightening of pulp and paper.

SUMMARY OF THE INVENTION

Applicants have identified cDNA clones that encode a novel xylanase referred to herein as XYL-IV and have certain sequence identity to previously-described xylanases.

In one embodiment, the invention provides an isolated nucleic acid molecule including DNA encoding XYL-IV. In certain aspects, the isolated nucleic acid includes DNA encoding an XYL-IV having the amino acid sequence of FIG. 2 (SEQ ID NO:2), or is complementary to such encoding nucleic acid sequences. Preferably, the DNA encoding a XYL-IV protein is derived from a microorganism, preferably a fungus or a bacterium. Preferably, the DNA is derived from a filamentous fungus such as Trichoderma spp., Humicola spp., Neurospora spp., Aspergillus spp., Fusarium spp., Penicillium spp., or Gliocladium spp., more preferably from Trichoderma spp. Also preferably, the DNA includes the nucleotide sequence of SEQ ID NO:1. Alternately, the DNA has at least 50%, 60%, or 70%, preferably at least 85% or 90%, sequence identity with the nucleotide sequence. of SEQ ID NO:1, or includes a derivative of the nucleotide sequence of SEQ ID NO:1, wherein the DNA encodes a XYL-IV protein which cleaves xylan, branched xylan or xylooligosaccharides. Vectors including such DNA, host cells having been transformed with such vectors and fermentation broths produced by such transformed host cells are also within the scope of the present invention.

Another embodiment of the present invention provides a partially or wholly isolated XYL-IV protein. Preferably, the XYL-IV is derived from a microorganism, preferably a fungus or a bacterium. Preferably, the XYL-IV is derived from a filamentous fungus, more preferably from a filamentous fungus such as Trichoderma spp., Humicola spp., Neurospora spp., Aspergillus spp., Fusarium spp., Penicillium spp., or Gliocladium spp., and most preferably from Trichoderma spp. In particular, the invention provides isolated native sequence XYL-IV, which in one embodiment, includes an amino acid sequence including residues 1 to 465 of FIG. 2 (SEQ ID NO:2). In a preferred embodiment of the present invention, the XYL-IV includes an amino acid sequence of SEQ ID NO:2, has at least 50% or 70%, preferably at least 85% or 90%, sequence identity with the amino acid sequence of SEQ ID NO:2, or includes a derivative of the amino acid sequence of SEQ ID NO:2, wherein the XYL-IV cleaves xylan.

Yet another embodiment of the present invention provides a method of producing XYL-IV protein including the steps of (a) obtaining a host cell which has been transformed with a vector including DNA encoding a XYL-IV protein; (b) culturing the host cell under conditions suitable for the expression and, optionally, secretion, of the XYL-IV protein; and (c) recovering the fermentation broth containing the XYL-IV protein.

In another embodiment, the invention provides an antibody which specifically binds to a XYL-IV protein or a domain thereof. Optionally, the antibody is a monoclonal antibody. In a still further embodiment, the invention provides methods using the XYL-IV protein or DNA encoding the XYL-IV protein.

BRIEF DESCRIPTION OF THE DRAWINGS

FIG. 1 illustrates the nucleotide sequence (SEQ ID NO:1) of a cDNA clone obtained from *Trichoderma reesei* RNA after growth on a mixed carbon source.

FIG. 2 illustrates the predicted amino acid sequence (SEQ ID NO:2) for a novel XYL-IV from *Trichoderma reesei*.

FIGS. 3A–3C illustrates locations of restriction enzyme cleavage sites along the nucleotide sequence of FIG. 1 (SEQ ID NO:1).

FIG. 4 illustrates efficient hydrolysis of HexA$^3$Xyl$_3$. Values were taken from Table 5.

FIG. 5 illustrates production of reducing sugars by XYL-IV from xylan, MeGlcA-xylan, and arabinoxylan from rye. Each xylan was present at 5 g/L and the reaction was run at 40° C. and pH 4.

FIGS. 6a and 6b illustrate synergism of XYL-IV with each of XYL-I and -II. Product was measured as reducing sugar (FIG. 6a) and free xylose (FIG. 6b). Values were taken from Table 6.

FIGS. 7a–d illustrate synergism in stepwise action of XYL-I and XYL-IV. In FIGS. 7a and 7b the substrate was MeGlcA-xylan. In FIGS. 7c and 7d the substrate was rye arabinoxylan. Values were taken from Table 7.

DETAILED DESCRIPTION OF THE INVENTION

Definitions

It should be noted that, as used in this specification and the appended claims, the singular forms "a," "an," and "the" include plural referents unless the content clearly dictates otherwise. Thus, for example, reference to a composition containing "a compound" includes a mixture of two or more compounds. It should also be noted that the term "or" is generally employed in its sense including "and/or" unless the content clearly dictates otherwise. "Xylanase" means a protein or polypeptide domain of a protein or polypeptide derived from a microorganism, e.g. a fungus, bacterium, or from a plant or animal, and that has the ability to catalyze cleavage of xylan at one or more of various positions of xylan's carbohydrate backbone, including branched xylans and xylooligosaccharides. Under certain conditions, a xylanase can also catalyze synthesis of a sugar such as a xylan or xylooligosaccharide from smaller units. Three specific xylanases from T. reesei are known in the literature.

As used herein, "XYL-IV" refers to an enzyme having xylanase activity and that, typically, in its native or wild type form, lacks a cellulose binding domain. The XYL-IV of the invention includes the protein including residues 1 to 465 of FIG. 2 (SEQ ID NO:2), proteins having at least 50% or 70%, preferably at least 85% or 90%, sequence identity with the amino acid sequence of SEQ ID NO:2, or a derivative of the amino acid sequence of SEQ ID NO:2, wherein the XYL-IV cleaves xylan. The XYL-IV provided by the invention specifically excludes the three known xylanases of T. reesei, which are referred to as XYL-I, XYL-II (belonging to glycosyl hydrolase family 11), and XYL-III (belonging to glycosyl hydrolase family 10) and are described in Törrönen, et al. and Xu, et al., supra). It is believed that XYL-IV acts on xylan in a different manner than the three known T. reesei xylanases, but may also cleave certain of the same positions.

It is contemplated herein that XYL-IV may be derived from any of a variety of sources including a microorganism, e.g. a fungus or a bacterium, a plant, or an animal. Specifically, it is contemplated that microorganisms which possess cellulolytic capabilities will be excellent sources of XYL-IV protein. In a particularly preferred embodiment of the invention,. the XYL-IV is derived from Trichoderma spp., particularly *Trichoderma reesei*. However, also preferably, the XYL-IV and/or DNA encoding XYL-IV according to the present invention is derived from a fungus, such as, Absidia spp.; Acremonium spp.; Agaricus spp.; Anaeromyces spp.; Aspergillus spp., including *A. aculeatus*, *A. awamori*, *A. flavus*, *A. foetidus*, *A. fumaricus*, *A. fumigatus*, *A. nidulans*, *A. niger*, *A. oryzae*, *A. terreus* and *A. versicolor*; Aeurobasidium spp.; Cephalosporum spp.; Chaetomium spp.; Coprinus spp.; Dactyllum spp.; Fusarium spp., including *F. conglomerans*, *F. decemcellulare*, *F. javanicum*, *F. lini*, *F. oxysporum* and *F. solani*; Gliocladium spp.; Humicola spp., including *H. insolens* and *H. lanuginosa*; Mucor spp.; Neurospora spp., including *N. crassa* and *N. sitophila*; Neocallimaslix spp.; Orpinomyces spp.; Penicillium spp; Phanerochaete spp.; Phlebia spp.; Piromyces spp.; Rhizopus spp.; Schizophyllum spp.; Trametes spp.; Trichoderma spp., including *T. reesei, T reesei (longibrachiatum)* and *T viride*; and Zygorhynchus spp.

Preferably, XYL-IV proteins according to the present invention are isolated or purified. By purification or isolation is meant the XYL-IV protein is altered from its natural state by virtue of separating the XYL-IV from some or all of the naturally occurring constituents with which it is associated in nature. Such isolation or purification may be accomplished by art recognized separation techniques such as ion exchange chromatography, affinity chromatography, hydrophobic separation, dialysis, protease treatment, ammonium sulphate precipitation or other protein salt precipitation, centrifugation, size exclusion chromatography, filtration, microfiltration, gel electrophoresis or separation on a gradient to remove whole cells, cell debris, impurities, extraneous proteins, or enzymes undesired in the final composition. It is further possible to then add constituents to the XYL-IV containing composition which provide additional benefits, for example, activating agents, anti-inhibition agents, desirable ions, compounds to control pH or other enzymes. Preferably, XYL-IV proteins according to the present invention are produced by recombinant methods.

As used herein, "microorganism" refers to a bacterium, a fungus, a virus, a protozoan, and other microbes or microscopic organisms. As used herein, "plant" refers to any member of the kingdorni Plantae. As used herein, "animal" refers to any member of the kingdom Animalia. Animals can be either single celled or multicellular.

As used herein, "derivative" means a protein which is derived from a precursor protein (e.g., the native protein) by addition of one or more amino acids to either or both the C- and N-terminal end, substitution of one or more amino acids at one or a number of different sites in the amino acid sequence, deletion of one or more amino acids at either or both ends of the protein or at one or more sites in the amino acid sequence, or insertion of one or more amino acids at one or more sites in the amino acid sequence. The preparation of a XYL-IV derivative is preferably achieved by modifying a DNA sequence which encodes the native protein, transformation of that DNA sequence into a suitable host, and expression of the modified DNA sequence to form the derivative XYL-IV.

"Derivatives" of the invention include peptides including altered amino acid sequences in comparison with a precursor amino acid sequence (e.g., a wild type or native state XYL-IV), wherein the peptides retain a characteristic XYL-IV nature of the precursor XYL-IV but have altered properties in some specific aspect. For example, a XYL-IV derivative may have an increased pH optimum or increased temperature or oxidative stability but retains its characteristic xylan modification activity. Similarly, derivatives according to the present invention include a cellulose binding domain which has either been added, removed or modified in such a way so as to significantly impair or enhance its cellulose binding ability. A derivative according to the present invention includes a xylan, or other substrate, binding domain, which has been added or modified to alter its substrate binding ability. It is contemplated that derivatives according to the present invention are derived from a DNA fragment encoding a XYL-IV derivative wherein the functional activity of the expressed XYL-IV derivative is retained. Derivatives further include chemical modifications that change the characteristics of the XYL-IV.

Ordinarily, a XYL-IV derivative will have at least about 50%, 70%, or 85% amino acid sequence identity, preferably at least about 85% amino acid sequence identity, more preferably at least about 90% amino acid sequence identity, even more preferably at least about 95% amino acid sequence identity and yet more preferably 98% amino acid sequence identity with the amino acid sequence of FIG. 2 (SEQ ID NO:2). Preferably, any amino acid substitutions are "conservative amino acid substitutions" using L-amino acids, wherein one amino acid is replaced by another biologically similar amino acid. Conservative amino acid substitutions are those that preserve the general charge, hydrophobicity/hydrophilicity, and/or steric bulk of the amino acid being substituted. Examples of conservative substitutions are those between the following groups: Gly/Ala, Val/Ile/Leu, Lys/Arg, Asn/Gln, Glu/Asp, Ser/Cys/Thr, and Phe/Trp/Tyr. A derivative may, for example, differ by as few as 1 to 10 amino acid residues, such as 6–10, as few as 5, as few as 4, 3, 2, or even 1 amino acid residue.

As used herein, a "native sequence XYL-IV" includes a polypeptide having the same amino acid sequence as a XYL-IV derived from nature. Such a native sequence XYL-FV can be isolated from nature or can be produced by recombinant or synthetic means. The term "native sequence XYL-IV" specifically encompasses naturally-occurring truncated or secreted forms of a XYL-IV and naturally-occurring variant forms (e.g., alternatively spliced forms) of a XYL-IV. In one embodiment of the invention, the native sequence XYL-IV includes amino acids 1 to 465 of FIG. 2 (SEQ ID NO:2).

As used herein, "percent (%) sequence identity" with respect to the amino acid or nucleotides sequences identified herein is defined as the percentage of amino acid residues or nucleotides in a candidate sequence that are identical with the amino acid residues or nucleotides in a XYL-IV sequence, after aligning the sequences and introducing gaps, if necessary, to achieve the maximum percent sequence identity, and not considering any conservative substitutions as part of the sequence identity.

Methods for performing sequence alignment and determining sequence identity are known to the skilled artisan, may be performed without undue experimentation, and calculations of identity values may be obtained with definiteness. See, for example, Ausubel et al., eds. (1995) *Current Protocols in Molecular Biology*, Chapter 19 (Greene Publishing and Wiley-lnterscience, New York); and the ALIGN program (Dayhoff (1978) in *Atlas of Protein Sequence and Structure* 5:Suppl. 3 (National Biomedical Research Foundation, Washington, D.C.). A number of algorithms are available for aligning sequences and determining sequence identity and include, for example, the homology alignment algorithm of Needleman et al. (1970) *J Mol. Biol* 48:443; the local homology algorithm of Smith et al. (1981) *Adv. Appl. Math.* 2:482; the search for similarity method of Pearson et al. (1988) *Proc. Natl. Acad. Sci.* 85:2444; the Smith-Waterman algorithm (*Meth. Mol. BioL* 70:173–187 (1997); and BLASTP, BLASTN, and BLASTX algorithms (see Altschul et al. (1990) *J Mol Biol.* 215:403–410). Computerized programs using these algorithms are also available, and include, but are not limited to: ALIGN or Megalign (DNASTAR) software, or WU-BLAST-2 (Altschul et al., *Meth. Enzym.,* 266:460–480 (1996)); or GAP, BESTFIT, BLAST Altschul et al., supra, FASTA, and TFASTA, available in the Genetics Computing Group (GCG) package, Version 8, Madison, Wis., USA; and CLUSTAL in the PC/Gene program by Intelligenetics, Mountain View, Calif. Those skilled in the art can determine appropriate parameters for measuring alignment, including algorithms needed to achieve maximal alignment over the length of the sequences being compared. Preferably, the sequence identity is determined using the default parameters determined by the program. Specifically, sequence identity can be determined by the Smith-Waterman homology search algorithm (*Meth. MoL Biol.* 70:173–187 (1997)) as implemented in MSPRCH program (Oxford Molecular) using an affine gap search with the following search parameters: gap open penalty of 12, and gap extension penalty of 1. Preferably, paired amino acid comparisons can be carried out using the GAP program of the GCG sequence analysis software package of Genetics Computer Group, Inc., Madison, Wis., employing the blosum62 amino acid substitution matrix, with a gap weight of 12 and a length weight of 2.

With respect to optimal alignment of two amino acid sequences, the contiguous segment of the variant amino acid sequence may have additional amino acid residues or deleted amino acid residues with respect to the reference amino acid sequence. The contiguous segment used for comparison to the reference amino acid sequence will include at least 20 contiguous amino acid residues, and may be 30, 40, 50, or more amino acid residues. Corrections for increased sequence identity associated with inclusion of gaps in the derivative's amino acid sequence can be made by assigning gap penalties.

As used herein, "expression vector" means a DNA construct including a DNA sequence which is operably linked to a suitable control sequence capable of affecting the expression of the DNA in a suitable host. Such control sequences may include a promoter to affect transcription, an optional operator sequence to control transcription, a sequence encoding suitable ribosome-binding sites on the MRNA, and sequences which control termination of transcription and translation. Different cell types are preferably used with different expression vectors. A preferred promoter for vectors used in *Bacillus subtilis* is the AprE promoter; a preferred promoter used in *E. coli* is the Lac promoter, a preferred promoter used in Saccharomyces cerevisiae is PGK1, a preferred promoter used in *Aspergillus niger* is glaA, and a preferred promoter for *Trichoderma reesei* is cbhI. The vector may be a plasmid, a phage particle, or simply a potential genomic insert. Once transformed into a suitable host, the vector may replicate and function independently of the host genome, or may, under suitable conditions, integrate into the genome itself. In the present specification, plasmid and vector are sometimes used interchangeably. However, the invention is intended to include other forms of expression vectors which serve equivalent functions and which are, or become, known in the art. Thus, a wide variety of host/expression vector combinations may be employed in expressing the DNA sequences of this invention. Useful expression vectors, for example, may consist of segments of chromosomal, non-chromosomal and synthetic DNA sequences such as various known derivatives of SV40 and known bacterial plasmids, e.g., plasmids from *E. coli* including col E1, pCR1, pBR322, pMb9, pUC 19 and their derivatives, wider host range plasmids, e.g., RP4, phage DNAs e.g., the numerous derivatives of phage λ, e.g., NM989, and other DNA phages, e.g., M13 and filamentous single stranded DNA phages, yeast plasmids such as the 2μ plasmid or derivatives thereof, vectors useful in eukaryotic cells, such as vectors useful in animal cells and vectors derived from combinations of plasmids and phage DNAs, such as plasmids which: have been modified to employ phage DNA or other expression control sequences. Expression techniques using the expression vectors of the present invention are known in the art and are described generally in, for example, Sambrook, et al., MOLECULAR CLONING: A LABORATORY MANUAL, SECOND EDITION, Cold Spring Harbor Press (1989). Often, such expression vectors including the DNA sequences of the invention are transformed into a unicellular host by direct insertion into the genome of a particular species through an integration event (see e.g., Bennett & Lasure, MORE GENE MANIPULATIONS IN FUNGI, Academic Press, San Diego, pp. 70–76 (1991) and articles cited therein describing targeted genomic insertion in fungal hosts).

As used herein, "host strain" or "host cell" means a suitable host for an expression vector including DNA according to the present invention. Host cells useful in the present invention are generally prokaryotic or eukaryotic hosts, including any transformable microorganism in which expression can be achieved. Specifically, host strains may be *Bacillus subtilis, Escherichia coli, Trichoderma reesei, Saccharomyces cerevisiae* or *Aspergillus niger*. Host cells are transformed or transfected with vectors constructed using recombinant DNA techniques. Such transformed host cells are capable of both replicating vectors encoding XYL-IV and its derivatives or variants (mutants) or expressing the desired peptide product. In a preferred embodiment according to the present invention, "host cell" means both the cells and protoplasts created from the cells of Trichoderma sp.

As used herein, "signal sequence" means a sequence of amino acids bound to the N-terminal portion of a protein which facilitates the secretion of the mature form of the protein outside of the cell. This definition of a signal sequence is a functional one. The mature form of the extracellular protein lacks the signal sequence which is cleaved off during the secretion process.

As used herein, "functionally attached" or "operably linked" means that a regulatory region, such as a promoter, terminator, secretion signal or enhancer region is attached to or linked to a structural gene and controls the expression of that gene.

"Stringency" of hybridization reactions is readily determinable by one of ordinary skill in the art, and generally is an empirical calculation dependent upon probe length, washing temperature, and salt concentration. In general, longer probes require higher temperatures for proper annealing, while shorter probes need lower temperatures. Hybridization generally-depends on the ability of denatured DNA to reanneal when complementary strands are present in an environment below their melting temperature. The higher the degree of desired homology between the probe and hybridizable sequence, the higher the relative temperature that can be used. As a result, it follows that higher relative temperatures would tend to make the reaction conditions more stringent, while lower temperatures less so. For additional details and explanation of stringency of hybridization reactions, see Ausubel et al., *Current Protocols in Molecular Biology* (Wiley Interscience Publishers, 1995).

As used herein, "stringent conditions" or "high-stringency conditions" can be identified by those that: (1) employ low ionic strength and high temperature for washing, for example, 0.015 M sodium chloride/0.0015 M sodium citrate/0.1% sodium dodecyl sulfate at 50° C.; (2) employ during hybridization a denaturing agent, such as formamide, for example, 50% (v/v) formamide with 0.1% bovine serum albumin/0.1% Ficoll/0.1% polyvinylpyrrolidone/50 mM sodium phosphate buffer at pH 6.5 with 750 mM sodium chloride, 75 mM sodium citrate at 42° C.; or (3) employ 50% formamide, 5×SSC (0.75 M NaCl, 0.075 M sodium citrate), 50 mM sodium phosphate (pH 6.8), 0.1% sodium pyrophosphate, 5×Denhardt's solution, sonicated salmon sperm DNA (50 μg/ml), 0.1% SDS, and 10% dextran sulfate at 42° C., with washes at 42° C. in 0.2×SSC (sodium chloride/sodium citrate) and 50% formamide at 55° C., followed by a high-stringency wash consisting of 0.1×SSC containing EDTA at 55° C.

As used herein, "moderately-stringent conditions" can be identified as described by Sambrook et al., *Molecular Cloning: A Laboratory Manual* (New York: Cold Spring Harbor Press, 1989), and include the use of washing solution and hybridization conditions (e.g., temperature, ionic strength, and %SDS) less stringent than those described above. An example of moderately stringent conditions is overnight incubation at 37° C. in a solution comprising: 20% formamide, 5×SSC (150 mM NaCl, 15 mM trisodium citrate), 50 mM sodium phosphate (pH 7.6), 5×Denhardt's solution, 10% dextran sulfate, and 20 mg/mL denatured sheared salmon sperm DNA, followed by washing the filters in 1×SSC at about 37–50° C. The skilled artisan will recognize how to adjust the temperature, ionic strength, etc. as necessary to accommodate factors such as probe length and the like.

As used herein, a substance (e.g. a polynucleotide or protein) "derived from" a microorganism means that the substance is native to the microorganism.

XYL-IV Specificity

In general, XYL-IV exhibits specificity different from that of a family 11 or a family 10 glycosyl hydrolase. In particular, XYL-IV exhibits specificity for substrates different from that of an α-arabinofuranosidase, an α-galactosidase, a β-xylosidase, a β-mannosidase. More particularly, XYL-IV cleaves substrates with a specificity different from XYL-I or -II or -III, That is, XYL-IV may cleave xylan at some of the same positions as these other xylanases, but it also cleaves at different positions.

In one embodiment, under typical reaction conditions, XYL-IV can exhibit greater activity toward an unsubstituted xylan or an acetylated MeGlcA-xylan, than do XYL-I or XYL-II. Both XYLs-IV and -II can hydrolyze deacetylated MeGlcA-xylan. XYL-II typically exhibits greater activity than XYL-IV toward an arabinoxylan. In cleavage of unsubstituted xylan or an acetylated MeGlcA-xylan, XYL-IV produced xylose as its main product, with lesser amounts of xylobiose and substituted xylo-oligosaccharides. The other two xylanases made different products. XYL-IV will generally cleave closer to a substituted xylose unit than either XYL-I or -II.

The difference in specificity between XYL-IV and XYLs-I and -II can yield synergy in cleavage of a product by combinations or mixtures of these enzymes. For example, cleavage of a substrate by a mixture of XYL-IV with XYL-I and/or XYL-II can result in a more than additive increase in the rate and/or extent of cleavage of the substrate compared to cleavage by fewer of these enzymes. Similarly, cleavage of a substrate by one or more of XYLs-I, -II and/or -IV followed by cleavage by a different XYL or combination of XYL-I, -II and/or -IV can result in a more than additive increase in the rate and/or extent of cleavage of the substrate compared to cleavage by fewer of these enzymes.

In one embodiment, XYL-IV can cleave several polymeric xylans from rye, unsubstituted xylan, MeGlcA-xylan, and arabinoxylan. Typically, XYL-IV cleaves arabinoxylan more slowly than the other two xylans, which can be cleaved at approximately equal rates. XYL-IV can hydrolyze both linear and substituted oligosaccharides. XYL-IV, under typical reaction conditions, does not cleave, or cleaves only poorly a glucomannan, a galactomannan, a β-glucan, a carboxymethyl cellulose, a laminarin, or a xylobiose.

In another embodiment, XYL-IV can be employed under certain reaction conditions to catalyze the coupling of sugars to form larger sugars. For example, XYL-IV can be employed for synthesis of a xylobiose or a xylooligosaccharide from smaller units. Alternatively, XYL-IV can catalyze formation of sugar derivatives from smaller units.

Preparation of XYL-IV

The present invention relates to the expression, isolation and use of XYL-IV and derivatives of XYL-IV. The XYL-IV or derivative is preferably prepared by recombinant methods. However, XYL-IV proteins for use in the present invention may be obtained by other art recognized means such as purification from natural isolates or chemical synthesis.

Purification from Natural Isolates

XYL-IV can be purified from natural isolates by known and commonly employed methods. For example, cells containing XYL-IV can be disrupted by various physical or chemical means, such as freeze-thaw cycling, sonication, mechanical disruption, or cell lysing agents. The XYL-IV can be recovered from the medium by conventional techniques including separations of the cells from the medium by centrifugation, filtration, and precipitation of the proteins in the supernatant or filtrate with a salt, for example, ammonium sulphate. The XYL-IV can then be purified from the disrupted cells by procedures such as: fractionation on an ion-exchange column; ethanol precipitation; reverse phase HPLC; chromatography on silica-based materials or on a ion-exchange resin such as DEAE; chromatofocusing; SDS-PAGE; ammonium sulfate precipitation; gel filtration using, for example, Sephadex G-75; and affinity chromatography. Various methods of protein purification may be employed and such methods are known in the art and described for example in Deutscher, *Methods in Enzymology* 182 (1990); Scopes, PROTEIN PURIFICATION: PRINCIPLES AND PRACTICE, Springer-Verlag, N.Y. (1982). The purification step(s) selected will depend, for example, on the particular XYL-IV produced or on the source of this enzyme.

Chemical Synthesis

Alternatively, the XYL-IV sequence, or portions thereof, may be produced by direct peptide synthesis using solid-phase techniques (see, e.g., Stewart, et al., SOLID-PHASE PEPTIDE SYNTHESIS, W. H. Freeman Co., San Francisco, Calif. (1969); Merrifield, *J Am. Chem. Soc.* 85:2149–2154 (1963)). In vitro protein synthesis may be performed using manual techniques or by automation. Automated synthesis may be accomplished, for instance, using an Applied Biosystems Peptide Synthesizer (Foster City, Calif.) using manufacturer's instructions. Various portions of XYL-IVs may be chemically synthesized separately and combined using chemical or enzymatic methods to produce a full-length XYL-IV.

Recombinant Methods

Isolation of DNA Encoding the XYL-IV

DNA encoding a XYL-IV may be obtained from a cDNA library prepared from a microorganism believed to possess the XYL-IV MRNA and to express it at a detectable level. The XYL-IV-encoding gene may also be obtained from a genomic library or by oligonucleotide synthesis.

Libraries can be screened with probes (such as antibodies to a XYL-IV or oligonucleotides of at least about 20–80 bases) designed to identify the gene of interest or the protein encoded by it. Screening the cDNA or genomic library with the selected probe may be conducted using standard procedures, such as described in Sambrook, et al., supra. An alternative means to isolate the gene encoding XYL-IV is to use PCR methodology (Sambrook, et al., supra; Dieffenbach, et al., PCR PRIMER:A LABORATORY MANUAL (Cold Spring Harbor Laboratory Press, 1995)).

In known techniques for screening a cDNA library, the oligonucleotide sequences selected as probes should be of sufficient length and sufficiently unambiguous that false positives are minimized. The oligonucleotide is preferably labeled such that it can be detected upon hybridization to DNA in the library being screened. Methods of labeling are well known in the art, and include the use of radiolabels like $^{32}$P-labeled ATP, biotinylation or enzyme labeling. Hybridization conditions, including moderate stringency and high stringency, are provided in Sambrook, et al., supra.

Sequences identified in such library screening methods can be compared and aligned to other known sequences deposited and available in public databases such as GenBank or other private sequence databases. Sequence identity (at either the amino acid or nucleotide level) within defined regions of the molecule or across the full-length sequence can be determined through sequence alignment using computer software programs such as ALIGN, DNAstar, and INMERIT, which employ various algorithms to measure homology.

Nucleic acid having a protein coding sequence may be obtained by screening selected cDNA or genomic libraries using the deduced amino acid sequence disclosed herein for the first time, and, if necessary, using conventional primer extension procedures as described in Sambrook, et al., supra, to detect precursors and processing intermediates of mRNA that may not have been reverse-transcribed into cDNA.

Selection and Transformation of Host Cells

Host cells are transfected or transformed with expression or cloning vectors described herein for XYL-IV production. The host cells are cultured in conventional nutrient media modified as appropriate for inducing promoters, selecting transformants, or amplifying the genes encoding the desired sequences. The culture conditions, such as media, temperature, pH and the like, can be selected by the skilled artisan without undue experimentation. In general, principles, protocols, and practical techniques for maximizing the productivity of cell cultures can be found in MAMMALIAN CELL BIOTECHNOLOGY: A PRACTICAL APPROACH, M. Butler, ed. (IRL Press, 1991) and Sambrook, et al., supra.

Methods of transfection are known to the ordinarily skilled artisan, for example, $CaPO_4$ and electroporation. Depending on the host cell used, transformation is performed using standard techniques appropriate to such cells. The calcium treatment employing calcium chloride, as described in Sambrook, et al., supra, or electroporation is generally used for prokaryotes or other cells that contain substantial cell-wall barriers. Infection with *Agrobacterium tumefaciens* is used for transformation of certain plant cells, as described by Shaw, et al., Gene 23:315 (1983) and WO 89/05859 published Jun. 29, 1989. Transformations into yeast can be carried out according to the method of Van Solingen, et al., *J. Bacteriol.* 130:946 (1977) and Hsiao, et al., *Proc. Nat'l Acad. Sci.* (USA) 76:3829 (1979). However, other methods for introducing DNA into cells, such as by nuclear microinjection, electroporation, microporation, biolistic bombardment, bacterial protoplast fusion with intact cells, or polycations, e.g., polybrene, polyornithine, may also be used.

Suitable host cells for cloning or expressing the DNA in the vectors herein include prokaryote, yeast, or filamentous fungal cells. Suitable prokaryotes include but are not limited to eubacteria, such as Gram-negative or Gram-positive organisms, for example, Enterobacteriaceae such as *E. coli*. Various *E. coli* strains are publicly available, such as *E. coli* K12 strain MM294 (ATCC 31,446); *E. coli* X1776 (ATCC 31,537); *E. coli* strain W3110 (ATCC 27,325) and K5 772 (ATCC 53,635). In addition to prokaryotes, eukaryotic microorganisms such as filamentous fungi or yeast are suitable cloning or expression hosts for vectors encoding XYL-IV. *Saccharomyces cerevisiae* is a commonly used lower eukaryotic host microorganism.

Preferably, the microorganism to be transformed includes a strain derived from Trichoderma spp. or Aspergillus spp. More preferably, the strain includes *T. reesei* which is useful for obtaining overexpressed protein or *Aspergillus niger* var. *awamori*. For example, Trichoderma strain RL-P37, described by Sheir-Neiss, et al. in *Appl. Microbiol. Biotechnol.* 20:46 (1984) is known to secrete elevated amounts of cellulase enzymes. Functional equivalents of RL-P37 include *Trichoderma reesei* (*longibrachiatum*) strain RUT-C30 (ATCC No. 56765) and strain QM9414 (ATCC No. 26921). Another example includes overproducing mutants as described in Ward, et al. in *Appl. Microbiol. Biotechnol.* 39:738 (1993). It is contemplated that these strains would also be useful in overexpressing Trichoderm spp. XYL-IV. The selection of the appropriate host cell is deemed to be within the skill in the art.

Selection and Transformation of Trichoderma sp. Host Cells

A preferred mode for preparing XYL-IV according to the present invention includes transforming a Trichoderma sp. host cell with a DNA construct including at least a fragment of DNA encoding a portion or all of the XYL-IV functionally attached to a promoter. The transformed host cell is then grown under conditions so as to express the desired protein. Subsequently, the desired protein product can be isolated or purified to substantial homogeneity.

Preferably, the microorganism to be transformed includes a strain derived from Trichoderma spp. More preferably, the strain includes *T. reesei* which is useful for obtaining overexpressed protein, Trichoderma strain RL-P37, functional equivalents of RL-P37, such as *Trichoderma reesei* (*longibrachiatum*) strain RUT-C30 (ATCC No. 56765), or strain QM9414 (ATCC No. 26921).

A selectable marker must be chosen so as to enable detection of the transformed fungus. Any selectable marker gene which is expressed in the selected microorganism will be suitable. For example, with Trichoderma sp., the selectable marker is chosen so that the presence of the selectable marker in the transformants will not significantly affect the properties thereof. Such a selectable marker may be a gene which encodes an assayable product. For example, a functional copy of a Trichoderma sp. gene may be used which if lacking in the host strain results in the host strain displaying an auxotrophic phenotype.

In a preferred embodiment, apyr4⁻ derivative strain of Trichoderma sp. is transformed with a functional pyr4 gene, which thus provides a selectable marker for transformation. A pyr4⁻ derivative strain may be obtained by selection of Trichoderma sp. strains which are resistant to fluoroorotic acid (FOA). The pyr4 gene encodes orotidine-5'-monophosphate decarboxylase, an enzyme required for the biosynthesis of uridine. Strains with an intact pyr4 gene grow in a medium lacking uridine but are sensitive to fluoroorotic acid. It is possible to select pyr4⁻ derivative strains which lack a functional orotidine monophosphate decarboxylase enzyme and require uridine for growth by selecting for FOA resistance. Using the FOA selection technique it is also possible to obtain uridine requiring strains which lack a functional orotate pyrophosphoribosyl transferase. It is possible to transform these cells with a functional copy of the gene encoding this enzyme (Berges and Barreau, *Curr. Genet.* 19:359 (1991)). Selection of derivative strains is easily performed using the FOA resistance technique referred to above, and thus, the pyr4 gene is preferably employed as a selectable marker.

To transform pyr4⁻ Trichoderma sp. so as to have the ability to express one or more xyl4 genes, a single DNA fragment including a xyl4 gene is then isolated from the deletion plasmid and used to transform an appropriate pyr⁻ Trichoderma host. Transformants are then identified and selected based on their ability to express the pyr4 gene product and thus compliment the uridine auxotrophy of the host strain. Southern blot analysis is then carried out on the resultant transformants to identify and confirm a double crossover integration event which replaces part or all of the coding region of the genomic copy of the gene to be deleted with the pyr4 selectable markers.

Although the specific plasmid vectors described above relate to preparation of pyr⁻ transformants, the present invention is not limited to these vectors. Various genes can be deleted and replaced in the Trichoderma sp. strain using the above techniques. In addition, any available selectable markers can be used, as discussed above. In fact, any Trichoderma sp. gene which has been cloned, and thus identified, can be deleted from or replaced in the genome using the above-described strategy.

As stated above, preferred host strains include derivatives of Trichoderma sp. which lack or have a nonfunctional gene or genes corresponding to the selectable marker chosen. For example, if the selectable marker of pyr4 is chosen, then a specific pyr4⁻ derivative strain is used as a recipient in the transformation procedure. Similarly, selectable markers including Trichoderma sp. genes equivalent to the *Aspergillus nidulans* genes amdS, argB, trpC, niaD may be used. The corresponding recipient strain must therefore be a derivative strain such as argB⁻, trpC⁻, niaD⁻, respectively.

In the preferred transformation technique, it must be taken into account that the permeability of the cell wall to DNA in Trichoderma sp. is very low. Accordingly, uptake of the desired DNA sequence, gene or gene fragment is at best minimal. There are a number of methods to increase the permeability of the Trichoderma sp. cell wall in the derivative strain (i.e., lacking a functional gene corresponding to the used selectable marker) prior to the transformation process.

The preferred method in the present invention to prepare Trichoderma sp. for transformation involves the preparation of protoplasts from fungal mycelium. The mycelium can be obtained from germinated vegetative spores. The mycelium is treated with an enzyme which digests the cell wall resulting in protoplasts. The protoplasts are then protected by the presence of an osmotic stabilizer in the suspending medium. These stabilizers include sorbitol, mannitol, potassium chloride, magnesium sulfate and the like. Usually the concentration of these stabilizers varies between 0.8 M to 1.2 M. It is preferable to use about a 1.2 M solution of sorbitol in the suspension medium.

Uptake of the DNA into the host Trichoderma sp. strain is dependent upon the calcium ion concentration. Generally between about 10 mM CaCl$_2$ and 50 mM CaCl$_2$ is used in an uptake solution. Besides the need for the calcium ion in the uptake solution, other items generally included are a buffering system such as TE buffer (10 Mm Tris, pH 7.4; 1 mM EDTA) or 10 mM MOPS, pH 6.0 buffer (morpholinepropanesulfonic acid) and polyethylene glycol (PEG). It is believed that the polyethylene glycol acts to fuse the cell membranes thus permitting the contents of the medium to be delivered into the cytoplasm of the Trichoderma sp. strain and the plasmid DNA is transferred to the nucleus. This fusion frequently leaves multiple copies of the plasmid DNA tandemly integrated into the host chromosome.

Usually a suspension containing the Trichoderma sp. protoplasts or cells that have been subjected to a permeability treatment at a density of $10^8$ to $10^9$/ml, preferably $2 \times 10^8$/ml are used in transformation. A volume of 100 microliters of these protoplasts or cells in an appropriate solution (e.g., 1.2 M sorbitol; 50 mM CaCl$_2$) are mixed with the desired DNA. Generally a high concentration of PEG is added to the uptake solution. From 0.1 to 1 volume of 25% PEG 4000 can be added to the protoplast suspension. However, it is preferable to add about 0.25 volumes to the protoplast suspension. Additives such as dimethyl sulfoxide, heparin, spermidine, potassium chloride and the like may also be added to the uptake solution and aid in transformation.

Generally, the mixture is then incubated at approximately 0°C. for a period of between 10 to 30 minutes. Additional PEG is then added to the mixture to further enhance the uptake of the desired gene or DNA sequence. The 25% PEG 4000 is generally added in volumes of 5 to 15 times the volume of the transformation mixture; however, greater and lesser volumes may be suitable. The 25% PEG 4000 is preferably about 10 times the volume of the transformation mixture. After the PEG is added, the transformation mixture is then incubated at room temperature before the addition of a sorbitol and CaCl$_2$ solution. The protoplast suspension is then further added to molten aliquots of a growth medium. This growth medium permits the growth of transformants only. Any growth medium can be used in the present invention that is suitable to grow the desired transformants. However, if Pyr$^+$ transformants are being selected it is preferable to use a growth medium that contains no uridine. The subsequent colonies are transferred and purified on a growth medium depleted of uridine.

At this stage, stable transformants may be distinguished from unstable transformants by their faster growth rate and the formation of circular colonies with a smooth, rather than ragged outline on solid culture medium lacking uridine. Additionally, in some cases a further test of stability may made by growing the transformants on solid non-selective medium (i.e. containing uridine), harvesting spores from this culture medium and determining the percentage of these spores which will subsequently germinate and grow on selective medium lacking uridine.

Preparation and Use of a Replicable Vector

DNA encoding the XYL-IV protein is prepared for insertion into an appropriate microorganism. According to the present invention, DNA encoding for a XYL-IV enzyme includes all of the DNA necessary to encode for a protein which has functional XYL-IV activity. Accordingly, DNA may be derived from any microbial source which produces XYL-IV, provided that the gene may be identified and isolated pursuant to the methods described herein. In a preferred embodiment, the DNA encodes for an XYL-IV protein derived from Trichoderma sp., and more preferably from *Trichoderma reesei*.

The DNA encoding the XYL-IV may be prepared by the construction of an expression vector carrying the DNA encoding the XYL-IV. The expression vector carrying the inserted DNA fragment encoding the XYL-IV may be any vector which is capable of replicating autonomously in a given host organism or of integrating into the DNA of the host, typically a plasmid, cosmid, viral particle, or phage. Various vectors are publicly available. It is also contemplated that more than one copy of DNA encoding a XYL-IV may be recombined into the strain to facilitate overexpression.

In preferred embodiments two types of expression vectors for obtaining expression of genes are contemplated. The first contains DNA sequences in which the promoter, gene coding region, and terminator sequence all originate from the gene to be expressed. Gene truncation may be obtained by deleting away undesired DNA sequences (e.g., coding for unwanted domains) to leave the domain to be expressed under control of its own transcriptional and translational regulatory sequences. A selectable marker is also contained on the vector allowing the selection for integration into the host of multiple copies of the novel xyl4 gene sequences.

The second type of expression vector is preassembled and contains sequences required for high level transcription and a selectable marker. It is contemplated that the coding region for a gene or part thereof can be inserted into this general purpose expression vector such that it is under the transcriptional control of the expression cassette's promoter and terminator sequences. For example, pTEX is such a general purpose expression vector. See U.S. Pat. No. 5,650,322 for a description of this vector. pTEX is a plasmid that has been designed as a multi-purpose expression vector for use in the filamentous fungus *T. reesei*. The expression cassette within the vector has several unique features that make it useful for this function. Transcription is regulated using the strong cbh1 gene promoter and terminator sequences for *T. reesei*.

In the vector, the DNA sequence encoding the XYL-IV of the present invention should be operably linked to transcriptional and translational sequences, i.e., a suitable promoter sequence and signal sequence in reading frame to the structural gene. The promoter may be any DNA sequence which shows transcriptional activity in the host cell and may be derived from genes encoding proteins either homologous or heterologous to the host cell. The signal peptide provides for extracellular production of the XYL-IV or derivatives thereof. The DNA encoding the signal sequence is preferably that which is naturally associated with the gene to be expressed, however the signal sequence from any suitable source, for example an exo-cellobiohydrolases or endoglucanase from Trichoderma, is contemplated in the present invention.

The appropriate nucleic acid sequence may be inserted into the vector by a variety of procedures. In general, DNA is inserted into an appropriate restriction endonuclease site (s) using techniques known in the art. Vector components generally include, but are not limited to, one or more of a signal sequence, an origin of replication, one or more marker genes, an enhancer element, a promoter, and a transcription termination sequence. Construction of suitable vectors containing one or more of these components employs standard ligation techniques which are known to the skilled artisan.

The desired XYL-IV, may be produced recombinantly not only directly, but also as a fusion polypeptide with a heterologous polypeptide, which may be a signal sequence or other polypeptide having a specific cleavage site at the N-terminus of the mature protein or polypeptide. In general, the signal sequence may be a component of the vector or it may be a part of the XYL-IV-encoding DNA that is inserted into the vector. The signal sequence may be a prokaryotic signal sequence selected, for example, from the group of the alkaline phosphatase, penicillinase, 1pp, or heat-stable enterotoxin II leaders. For yeast secretion the signal sequence may be, e.g., the yeast invertase leader, alpha factor leader (including Saccharomyces and Kluyveromyces α-factor leaders, the latter described in U.S. Pat. No. 5,010,182), or acid phosphatase leader, the *C. albicans* glucoamylase leader (EP 362,179 published Apr. 4, 1990), or the signal described in WO 90/13646 published Nov. 15, 1990.

Both expression and cloning vectors contain a nucleic acid sequence that enables the vector to replicate in one or more selected host cells. Such sequences are well known for a variety of bacteria, yeast, and viruses. The origin of replication from the plasmid pBR322 is suitable for most Gram-negative bacteria and the 2μ plasmid origin is suitable for yeast.

Expression and cloning vectors will typically contain a selection gene, also termed a selectable marker. Typical selection genes encode proteins that (a) confer resistance to antibiotics or other toxins, e.g., ampicillin, neomycin, methotrexate, or tetracycline, (b) complement auxotrophic deficiencies, or (c) supply critical nutrients not available from complex media, e.g., the gene encoding D-alanine racemase for Bacilli. A suitable selection gene for use in yeast is the trp1 gene present in the yeast plasmid YRp7 (Stinchcomb, et al., *Nature* 282:39 (1979); Kingsman, et al., *Gene* 7:141 (1979); Tschemper, et al., *Gene* 10:157 (1980)). The trp1 gene provides a selection marker for a mutant strain of yeast lacking the ability to grow in tryptophan, for example, ATCC No. 44076 or PEP4-1 (Jones, *Genetics* 85:12 (1977)). A preferred selection gene for use in Trichodernza sp is the pyr4 gene.

Expression and cloning vectors usually contain a promoter operably linked to the XYL-IV-encoding nucleic acid sequence. The promoter directs mRNA synthesis. Promoters recognized by a variety of potential host cells are well known. Preferred promoters include a fungal promoter sequence, for example, the promoter of the cbh1 or egl1 gene.

Promoters suitable for use with prokaryotic hosts include the β-lactamase and lactose promoter systems (Chang, et al., *Nature* 275:615 (1978); Goeddel, et al., *Nature*, 281:544 (1979)), alkaline phosphatase, a tryptophan (trp) promoter system (Goeddel, *Nucl. Acids Res.* 8:4057 (1980); and European patent application 36,776), and hybrid promoters such as the tac promoter (deBoer, et al., *Proc. Nat'l Acad. Sci. USA* 80:21 (1983)). Promoters for use in bacterial systems also will contain a Shine-Dalgarno (S.D.) sequence operably linked to the DNA encoding the XYL-IV.

Examples of suitable promoting sequences for use with yeast hosts include the promoters for 3-phosphoglycerate kinase (Hitzeman, et al., *J. Biol. Chem.* 255:2073 (1980)) or other glycolytic enzymes (Hess, et al., *J. Adv. Enzyme Reg.* 7:149 (1968); Holland, *Biochem.* 17:4900 (1978)), such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase. Other yeast promoters, which are inducible promoters having the additional advantage of transcription controlled by growth conditions, are the promoter regions for alcohol dehydrogenase 2, isocytochrome C, acid phosphatase, degradative enzymes associated with nitrogen metabolism, metallothionein, glyceraldehyde-3-phosphate dehydrogenase, and enzymes responsible for maltose and galactose utilization. Suitable vectors and promoters for use in yeast expression are further described in EP 73,657.

Expression vectors used in eukaryotic host cells (e.g., yeast, fungi, insect, plant) will also contain sequences necessary for the termination of transcription and for stabilizing the mRNA. Such sequences are commonly available from the 5' and, occasionally 3', untranslated regions of eukaryotic or viral DNAs or cDNAs. These regions contain nucleotide segments transcribed as polyadenylated fragments in the untranslated portion of the mRNA encoding XYL-IV.

Detecting Gene Amplification/Expression

Gene amplification and/or expression may be measured in a sample directly, for example, by conventional Southern blotting, Northern blotting to quantitate the transcription of mRNA (Thomas, *Proc. Nat'l Acad. Sci. USA* 77:5201 (1980)), dot blotting (DNA analysis), or in situ hybridization, using an appropriately labeled probe, based on the sequences provided herein. Alternatively, antibodies may be employed that can recognize specific duplexes, including DNA duplexes, RNA duplexes, and DNA-RNA hybrid duplexes or DNA-protein duplexes. The antibodies in turn may be labeled and the assay may be carried out where the duplex is bound to a surface, so that upon the formation of duplex on the surface, the presence of antibody bound to the duplex can be detected.

Gene expression, alternatively, may be measured by immunological methods, such as immunohistochemical staining of cells and assay of cell culture fluids, to quantitate directly the expression of gene product. Antibodies useful for immunohistochemical staining and/or assay of sample fluids may be either monoclonal or polyclonal, and may be prepared in any mammal. Conveniently, the antibodies may be prepared against a native sequence XYL-IV, against a synthetic peptide based on the DNA sequences provided herein, or against an exogenous sequence fused to XYL-IV-encoding DNA and encoding a specific antibody epitope.

Polypeptide Purification

Forms of XYL-IV may be recovered from culture medium or from host cell lysates by the methods described above for isolation and purification from natural isolates. Additional techniques can be used depending on the host cell employed and any variant structures in the recombinant enzyme. For example, if the recombinant enzyme is membrane-bound, it can be released from the membrane using a suitable-detergent solution (e.g. Triton-X 100) or by enzymatic cleavage. Purification of recombinant enzyme may also employ protein A Sepharose columns to remove contaminants such as IgG and metal chelating columns to bind epitope-tagged forms of the XYL-IV. The purification step(s) selected will depend, for example, on the nature of the production process used, the particular XYL-IV produced, and any variant structure for the recombinant enzyme.

Derivatives of XYL-IV

In addition to the native sequence XYL-IV described herein, it is contemplated that XYL-IV derivatives can be prepared with altered amino acid sequences. XYL-IV derivatives can be prepared by introducing appropriate nucleotide changes into the XYL-IV-encoding DNA, or by synthesis of the desired XYL-IV. Those skilled in the art will appreciate that amino acid changes may alter post-translational processes of the XYL-IV, such as changing the number or position of glycosylation sites.

Derivatives of the native sequence XYL-IV or of various domains of the XYL-IV described herein, can be made, for example, using any of the techniques and guidelines for conservative and non-conservative mutations set forth, for instance, in U.S. Pat. No. 5,364,934. Sequence variations may be a substitution, deletion or insertion of one or more codons encoding the XYL-IV that results in a change in the amino acid sequence of the XYL-IV as compared with the native sequence XYL-IV. Optionally, the sequence variation is by substitution of at least one amino acid with any other amino acid in one or more of the domains of the XYL-IV.

Guidance in determining which amino acid residue may be inserted, substituted or deleted without adversely affecting the desired XYL-IV activity may be found by comparing the sequence of the polypeptide-with that of homologous known protein molecules and minimizing the number of amino acid sequence changes made in regions of high homology. Amino acid substitutions can be the result of replacing one amino acid with another amino acid having similar structural and/or chemical properties, such as the replacement of a leucine with a serine, i.e., conservative amino acid replacements. Insertions or deletions may optionally be in the range of 1 to 5 amino acids. The variation allowed may be determined by systematically making insertions, deletions or substitutions of amino acids in the sequence and testing the resulting derivatives for functional activity using techniques known in the art.

The sequence variations can be made using methods known in the art such as oligonucleotide-mediated (site-directed) mutagenesis, alanine scanning, and PCR mutagenesis. Site-directed mutagenesis (Carter, et al., *Nucl. Acids Res.* 13:4331 (1986); Zoller, et al., *Nucl. Acids Res.* 10:6487 (1987)), cassette mutagenesis (Wells, et al., *Gene* 34:315 (1985)), restriction selection mutagenesis (Wells, et al., *Philos. Trans. R. Soc. London SerA* 317:415 (1986)) or other known techniques can be performed on the cloned DNA to produce the XYL-IV-encoding DNA with a variant sequence.

Scanning amino acid analysis can also be employed to identify one or more amino acids along a contiguous sequence. Among the preferred scanning amino acids are relatively small, neutral amino acids. Such amino acids include alanine, glycine, serine, and cysteine. Alanine is typically a preferred scanning amino acid among this group because it eliminates the side-chain beyond the beta-carbon and is less likely to alter the main-chain conformation of the derivative. Alanine is also typically preferred because it is the most common amino acid. Further, it is frequently found in both buried and exposed positions (Creighton, THE PROTEINS, (W. H. Freeman & Co., N.Y.); Chothia, *J Mol. Biol.*, 150:1 (1976)). If alanine substitution does not yield adequate amounts of derivative, an isosteric amino acid can be used.

Anti-XYL-IV-Antibodies

The present invention further provides anti-XYL-IV antibodies. Exemplary antibodies include polyclonal and monoclonal antibodies.

The anti-XYL-IV antibodies of the present invention may include polyclonal antibodies. Methods of preparing polyclonal antibodies are known to the skilled artisan. Polyclonal antibodies can be raised in a mammal, for example, by one or more injections of an immunizing agent and, if desired, an adjuvant. Typically, the immunizing agent and/or adjuvant will be injected in the mammal by multiple subcutaneous or intraperitoneal injections. For anti-XYL-IV antibodies, the immunizing agent may include the XYL-IV or a fusion protein thereof. It may be useful to conjugate the immunizing agent to a protein known to be immunogenic in the mammal being immunized. Examples of such immunogenic proteins include but are not limited to keyhole limpet hemocyanin, serum albumin, bovine thyroglobulin, and soybean trypsin inhibitor. Examples of adjuvants which may be employed include Freund's complete adjuvant and MPL-TDM adjuvant (monophosphoryl Lipid A, synthetic trehalose dicorynomycolate). The immunization protocol may be selected by one skilled in the art without undue experimentation.

The anti-XYL-IV antibodies may, alternatively, be monoclonal antibodies. Monoclonal antibodies may be prepared using hybridoma methods, such as those described by Kohler and Milstein, *Nature* 256:495 (1975). In a hybridoma method, a mouse, hamster, or other appropriate host animal, is typically immunized with an immunizing agent to elicit lymphocytes that produce or are capable of producing antibodies that will specifically bind to the immunizing agent. Alternatively, the lymphocytes may be immunized in vitro.

For anti-XYL-IV antibodies, the immunizing agent will typically include the XYL-IV or a fusion protein thereof Generally, either peripheral blood lymphocytes ("PBLs") are used if cells of human origin are desired, or spleen cells or lymph node cells are used if non-human mammalian sources are desired. The lymphocytes are then fused with an immortalized cell line using a suitable fusing agent, such as polyethylene glycol, to form a hybridoma cell (Goding, MONOCLONAL ANTIBODIES: PRINCIPLES AND PRACTICE, Academic Press, (1986) pp. 59–103). Immortalized cell lines are usually transformed mammalian cells, particularly myeloma cells of rodent, bovine and human origin. Usually, rat or mouse myeloma cell lines are employed. The hybridoma cells may be cultured in a suitable culture medium that preferably contains one or more substances that inhibit the growth or survival of the unfused, immortalized cells. For example, if the parental cells lack the enzyme hypoxanthine guanine phosphoribosyl transferase (HGPRT or HPRT), the culture medium for the hybridomas typically will include hypoxanthine, aminopterin, and thymidine ("HAT medium"), which substances prevent the growth of HGPRT-deficient cells.

Preferred immortalized cell lines are those that fuse efficiently, support stable high level expression of antibody by the selected antibody-producing cells, and are sensitive to a medium such as HAT medium. More preferred immortalized cell lines are murine myeloria lines, which can be obtained, for instance, from the Salk Institute Cell Distribution Center, San Diego, Calif. and the American Type Culture Collection, Manassas, Va. Human myeloma and mouse-human heteromyeloma cell lines also have been described for the production of human monoclonal antibodies (Kozbor, *J. Immunol.* 133:3001 (1984); Brodeur, et al., MONOCLONAL ANTIBODY PRODUCTION TECHNIQUES AND APPLICATIONS, Marcel Dekker, Inc., New York, (1987) pp. 51–63).

The culture medium in which the hybridoma cells are cultured can then be assayed for the presence of monoclonal antibodies directed against a XYL-IV. Preferably, the binding specificity of monoclonal antibodies produced by the hybridoma cells is determined by immunoprecipitation or by an in vitro binding assay, such as radioimmunoassay (RIA) or enzyme-linked immunoabsorbent assay (ELISA). Such techniques and assays are known in the art. The binding affinity of the monoclonal antibody can, for example, be determined by the Scatchard analysis of Munson and Pollard, *Anal. Biochem.* 107:220 (1980).

After the desired hybridoma cells are identified, the clones may be subcloned by limiting dilution procedures and grown by standard methods (Goding, supra). Suitable culture media for this purpose include, for example, Dulbecco's Modified Eagle's Medium and RPMI-1640 medium.

The monoclonal antibodies secreted by the subclones may be isolated or purified from the culture medium by conventional immunoglobulin purification procedures such as, for example, protein A-Sepharose, hydroxylapatite chromatography, gel electrophoresis, dialysis, or affinity chromatography.

The monoclonal antibodies may also be made by recombinant DNA methods, such as those described in U.S. Pat. No. 4,816,567. DNA encoding the monoclonal antibodies of the invention can be readily isolated and sequenced using conventional procedures (e.g., by using oligonucleotide probes that are capable of binding specifically to genes encoding the heavy and light chains of murine antibodies). The hybridoma cells of the invention serve as a preferred source of such DNA. Once isolated, the DNA may be placed into expression vectors, which are then transfected into host cells such as simian COS cells, Chinese hamster ovary (CHO) cells, or myeloma cells that do not otherwise produce immunoglobulin protein, to obtain the synthesis of monoclonal antibodies in the recombinant host cells. The DNA also may be modified, for example, by substituting the coding sequence for human heavy and light chain constant domains in place of the homologous murine sequences (U.S. Pat. No. 4,816,567; Morrison, et al., supra) or by covalently joining to the immunoglobulin coding sequence all or part of the coding sequence for a non-immunoglobulin polypeptide. Such a non-immunoglobulin polypeptide can be substituted for the constant domains of an antibody of the invention, or can be substituted for the variable domains of one antigen-combining site of an antibody of the invention to create a chimeric bivalent antibody.

The antibodies may be monovalent antibodies. Methods for preparing monovalent antibodies are well known in the art. For example, one method involves recombinant expression of immunoglobulin light chain and modified heavy chain. The heavy chain is truncated generally at any point in the Fc region so as to prevent heavy chain crosslinking. Alternatively, the relevant cysteine residues are substituted with another amino acid residue or are deleted so as to prevent crosslinking.

In vitro methods are also suitable for preparing monovalent antibodies. Digestion of antibodies to produce fragments thereof, particularly, Fab fragments, can be accomplished using routine techniques known in the art.

Methods Employing XYL-IV

In another embodiment, the xylanases of the present invention have applications in enhancing the delignification and/or the bleaching of pulp according to art-recognized techniques. The process includes contacting the pulp with XYL-IV and is dependent upon factors such as pH, temperature, treatment time, dosage of enzyme and the quantity and type of pulp.

It is preferred that the above process be carried out at a temperature and pH which will enhance the enzymatic activity of the XYL-IV. The preferred treatment period for applying the XYL-IV of the present invention is from about 10 minutes to about 4 hours depending upon factors such as the results desired, the quantity and quality of pulp treated and concentration of enzyme, for example.

A suitable enzyme dose is about 0.10 to 200 units/g of dry pulp more preferably 0.50 to 50 units/g. The xylanase activity of the enzyme preparations is determined as follows: To 1.8 ml of xylan solution (0.6% Sigma No. X-0627, prepared in 0.05 M sodium acetate buffer and adjusted to pH 5.3 with acetic acid), 0.200 ml of suitably diluted enzyme in the same buffer is added. The solution is incubated at 40° C. for exactly 30 minutes. The reaction is then stopped by adding 3 ml DNS reagent (3,5-dinitrosalicylate 10 f/l; Na,K tartrate 300 g/l), and the color is developed by boiling the sample for 5 minutes. The absorbency is then measured at a wave length of 540 nm. One enzyme unit liberates one micromole of reducing sugars calculated as xylose per minute under assay conditions. The activity is calculated from an enzyme dilution liberating 4 micromoles of reducing sugar under assay conditions. The activity of XYL-IV can also be stated in mass units, for example, a preferred amount of XYL-IV can be about 1 ppm to about 100,000 ppm in an assay or reaction mixture.

The present method may be applied to upgrade or assist in the upgrading of any of a wide variety of processed pulps, i.e., pulps which have been already previously treated in any of a variety of ways to reduce their lignin content and are treated in the process to further enhance the lignin removal by chemical methods. The present method may be applied to treat hardwood and softwood kraft pulps to enhance lignin removal and brightening of the pulps. The method is particularly applicable to chemical pulps, i.e., those in which the lignin component has been chemically modified by various chemical treatments such as in the sulfate (kraft) processes and oxygen delignification, and is preferably applied to kraft pulps. In a preferred method, the XYL-IV is applied to the pulp after kraft digestion or oxygen delignification but prior to bleaching. In the case where both kraft digestion and oxygen delignification are performed on the same pulp, the enzyme is applied after kraft digestion, prior to oxygen delignification or after oxygen delignification. The present invention is also applicable to ozone bleached pulps.

The resulting pulp is treated to remove the releasable lignin component using an appropriate extractant. In another embodiment, pulp treated with the XYL-IV may be subsequently treated with lignin-degrading chemicals such as chlorine, chlorine dioxide and peroxide, and further extracted with an appropriate extractant. In yet another embodiment, the enzyme treated pulp may be treated with an appropriate extractant, followed by lignin degradation and a final treatment with an appropriate extractant. Such extractants essentially solubilize the affected lignin component and suitable extractants include but are not limited to bases such as alkali metal hydroxides (E), DMF, dioxane, acetone, and alcohol. Hydroxide extractions may be combined with hydrogen peroxide ($E_p$) or oxygen ($E_p$). The resulting pulp may then be further bleached by a chemical bleaching sequence such as chlorine dioxide (DED) or peroxide (P—P) to the desired brightness whereby substantial savings of chemicals are observed when compared to pulp bleached to the same brightness by the same sequence but without using the enzyme treatment. Reduction of chlorine containing chemicals or peroxide is achieved in such a way. In addition, by performing the present invention with the above presented enzymes, one may apply the same amount of bleaching chemicals to the pulp and yet achieve a greater brightness in the treated pulp.

In another embodiment, the present invention provides for additional applications of the XYL-IV described above in a variety of industrial settings. For example, the XYL-IV may be used to enzymatically breakdown agricultural wastes for production of alcohol fuels and other important industrial chemicals, for production of animal or human foodstuffs, or as a component in a detergent composition.

The following examples are offered for illustrative purposes only, and are not intended to limit the scope of the present invention in any way. All patent and literature references cited in the present specification are hereby incorporated by reference in their entirety.

EXAMPLES

Example 1

*Trichoderma reesei* cDNA Clone Encoding a Novel Xylanase

FIG. 1 shows the nucleotide sequence (SEQ. ID:NO1) and predicted corresponding amino acid sequence (SEQ. ID:NO2) of a cDNA clone obtained from a library of cDNA prepared from *Trichoderma reesei* RNA after growth on a mixed carbon source by methods common in the art. An open reading frame of 1518 nucleotides was identified and the encoded protein was deduced. The mature protein was predicted to be 465 amino acids in length.

The XYL-IV identified above lacks the cellulose binding domain (CBD) of some of the cellulases produced by Trichoderma and other fungal cellulases. CBDs are also associated with some non-cellulolytic extracellular fungal enzymes such as acetyl xylan esterase and mannanase from *Trichoderma reesei* (*longibrachiatum*). The XYL-IV identified above also lacks a sequence having identity with the linker or hinge regions present in Trichoderma and other fungal cellulases and which connect the CBD with the catalytic domain.

Regions with sequence identity and sequence similarity are observed between the predicted amino acid sequence (SEQ ID NO:2) of the Trichoderma xylanase of FIG. 2 and known sequences of microbial glycosidases and certain sequences of unknown function. Identity and similarity were detected in a search of protein sequence databanks carried out with the program BLAST (Altschul, et al., *J Mol. Biol.* 215:403 (1990)) or another similar program known in the art. Sequence similarity was determined by standard methods.

In particular, paired amino acid comparisons were carried out using the GAP program of the GCG sequence analysis software package of Genetics Computer Group, Inc., Madison, Wis. Sequence similarity was determined by standard methods. This analysis of the amino acid sequence of the *T. reesei* XYL-IV is reported in Table 1 using the GAP program with the blosum62 amino acid substitution matrix, with a gap weight of 12 and a length weight of 2.

This analysis of the amino acid sequence of the *T. reesei* XYL-IV is reported in Table 1.

TABLE 1

Sequence Identity and Similarity Comparisons of XYL-IV

| | Amycolatopsis orientalis cosmid PCZA361 | Bacillus subtilus genome | Erwinia chrysanthemi xylanase gene | Aeromonas caviae xylanase D gene |
|---|---|---|---|---|
| T. reesei xylanse-4 | 38% identity 43% similarity | 25% identity 33% similarity | 29% identity 36% similarity | 23% identity 31% similarity |
| Amycolatopsis orientalis cosmid PCZA361 | | 29% identity 38% similarity | 24% identity 33% similarity | 28% identity 36% similarity |

TABLE 1-continued

Sequence Identity and Similarity Comparisons of XYL-IV

| | Amycolatopsis orientalis cosmid PCZA361 | Bacillus subtilus genome | Erwinia chrysanthemi xylanase gene | Aeromonas caviae xylanase D gene |
|---|---|---|---|---|
| Bacillus subtilus genome | | | 40% identity 49% similarity | 77% identity 82% similarity |
| Erwinia chrysanthemi xylanase gene | | | | 41% identity 49% similarity |

Example 2

Characterization of XYL-IV

The XYL-IV, or XYL IV, was characterized by several methods common for characterizing proteins and enzymes.

The XYL-IV from *Trichoderma reesei* was isolated. Upon polyacrylamide gel electrophoresis, this XYL-IV shows a molecular weight of approximately 43.0 kDa. This XYL-IV has several isoforms each with a pI of approximately 7, as determined by PHAST® system (Pharmacia). Slight staining by Schiffs reagent indicates only a low level of glycosylation. The XYL-IV gene was expressed when the *Trichoderma reesei* was grown on cellulose as the sole carbon source, but not when grown on glucose as the sole carbon source.

What is believed to be an N-terminal amino acid sequence of the mature XYL-IV was determined by Edman degradation after trypsin cleavage of the protein and isolation of peptides by C18 reverse phase HPLC. The N-terminal sequence was determined as: Xaa-Ser-Tyr-Ala-Thr-Xaa-Ser-Gln-Tyr-Xaa-Ala-Asn-Ile-Xaa-Ile- (SEQ ID NO:3) in which Xaa indicates an amino acid that remained unidentified due to insufficient signal.

XYL IV is homologous to xylanases that are classified as belonging to Family 5 of glycosyl hydrolases.

Employing a xylan substrate, which may not be the optimal substrate for XYL-IV, the pH optimum of XYL-IV activity was observed to be between pH 3.5 and 4. This differs from the pH optima for XYL-II, pH 5–5.5, and XYL 1, pH 3.5–4.5. At pH 4, XYL-IV showed highest activity levels at temperatures between 40 and 50° C. This enzyme retained activity in solution at room temperature for several hours, but slowly lost activity at elevated temperatures.

Substrate specificity of XYL-IV was determined for macromolecular substrates and p-nitrophenyl-glycosides. The following macromolecular substances were not significantly cleaved by XYL-IV after 24 hr at 40° C. at pH 4 in a sodium citrate buffer: glucomannan (konjac, Megazyme), galactomannan (locust bean, Sigma), β-glucan (barley, Megazyme), carboxymethyl cellulose (Fluka), laminarin (Sigma) or xylobiose. Employing known p-nitrophenyl-glycoside substrates, XYL-IV did not show activity expected for an α-arabinofuranosidase, an α-galactosidase, a β-xylosidase, or β-mannosidase.

The XYL-IV was further evaluated for hydrolysis of several substrates in the presence and absence of XYL-I and XYL-II. Table 2 describes the substrates employed in these studies. The monosaccharide composition of each substrate was analyzed by HPLC after complete enzymatic hydrolysis to monosaccharides.

TABLE 2

Substrates For The Hydrolysis Experiments

| Xylan | Plant | Source | Xylose (% of dw) | Arabinose (% of dw) | MeGlcA (% of dw) |
|---|---|---|---|---|---|
| Unsubstituted xylan | Beech | Lenzing AG | 100 | — | <2 |
| 4-O-MeGlcA-xylan | Birch | Roth | 86 | — | 9 |
| Ac-4-O-MeGlcA-xylan* | Birch | VTT | 69 | — | 5 |
| Arabinoxylan | Oat spelts | Sigma | 67 | 6 | <2 |
| Arabinoxylan** | Wheat | Megazyme | 63 | 21 | nd |
| Arabinoxylan | Rye | Megazyme | 43 | 25 | nd |

*Almost every second xylose unit carries an acetyl substituent.
**A small amount of unknown oligosaccharides was still present after complete enzymatic hydrolysis.
nd = not determined.

XYL-IV was compared to XYL-I and XYL-II in an experiment in which a small amount of each enzyme was employed and only a small proportion (typically <10%) of each substrate was hydrolyzed. Reducing sugars formed by the enzymes were assayed with the DNS method, which is known in the art. Linear xylo-oligosaccharides (1-mers to 5-mers, $Xyl_1$ to $Xyl_5$) were determined by HPLC using commercial oligosaccharides as standards. The hydrolysis was studied under conditions of: 24 hr, 40° C., pH 4.0 (XYL I and XYL IV) and pH 5.0 (XYL II). The results of these studies are shown in Table 3.

In these experiments, XYL-IV exhibited greater activity toward unsubstituted xylan and acetylated MeGlcA-xylan, compared to XYLs-I and -II. Both XYL-IV and -II hydrolyzed deacetylated MeGlcA-xylan. XYL-II exhibited greater activity than XYL-IV toward arabinoxylans. XYL-IV produced xylose as its main product, with lesser amounts of xylobiose and substituted xylo-oligosaccharides. The other two xylanases produced a very different product mixture (Table 3). The products and activity of XYL-IV were different from those of family 11 and family 10 glycosyl hydrolases.

Substrate specificity of XYL-IV was further characterized by employing several isolated oligosaccharide substrates (Table 4). The hydrolysis was studied under conditions of: pH 4.0, 40° C., 1h.

TABLE 4

Hydrolysis of Substituted Oligosaccharides (0.5–0.7 g/l) by XYL-IV of *T. reesei* (500 nkat/g)

| Oligosaccharides | Products |
|---|---|
| $HexA^2Xyl_2$ + $HexA^3Xyl_3$ | $HexA^2Xyl_2$ + Xyl |
| $Ara^2Xyl_3$* | No action |
| $Ara^2Xyl_4$ + $Ara^3Xyl_4$* | $AraXyl_3$ + $AraXyl_4$** |

*Structures published in Tenkanen et al. 1996.
**Most probably $Ara^2Xyl_3$ + $Ara^2Xyl_4$ In these experiments, XYL-IV cleaved the link between two unsubstituted xylose units, but not the link between a substituted and an unsubstituted xylose unit. XYL-IV did, however, cleave closer to the substituted unit than either XYL-I or -II. XYL-IV left only one unsubstituted unit on the reducing end of the oligosaccharide.

The amount of XYL-IV needed for efficient hydrolysis of $HexA^3Xyl_3$ was evaluated by incubating a mixture of

TABLE 3

Hydrolysis of Xylans (5 g/l) By XYLs-I, -II, and -IV of *Trichoderma reesei*.

| Substrate | Enzyme | Reducing Sugars (g/l) | Xyl (mg/l) | $Xyl_2$ (mg/l) | $Xyl_3$ (mg/l) | $Xyl_4$ (mg/l) | $Xyl_5$ (mg/l) | Total+ (mg/l) |
|---|---|---|---|---|---|---|---|---|
| Unsubstituted xylan | XYL I | — | <4 | <4 | <4 | <4 | <4 | <4 |
| | XYL II | 0.12 | <4 | <4 | 11 | 10 | 11 | 32 |
| | XYL IV | 0.44 | 430 | 93 | <4 | <4 | <4 | 523 |
| MeGlcA-xylan | XYL I | 0.18 | <4 | 7 | 16 | 13 | 16 | 52 |
| | XYL II | 0.49 | <4 | 68 | 110 | 71 | 65 | 314 |
| | XYL IV | 0.52 | 370 | 110 | <4 | <4 | <4 | 480 |
| Ac-MeGlcA-xylan* | XYL I | 1.08 | 63 | 110 | 220 | 190 | 240 | 823 |
| | XYL II | 0.65 | 7 | 67 | 72 | 75 | 100 | 321 |
| | XYL IV | 1.16 | 170 | 1040 | 200 | 26 | 21 | 1457 |
| Oat spelt arabinoxylan | XYL I | 0.17 | <4 | 6 | 13 | 11 | 11 | 41 |
| | XYL II | 0.81 | <4 | 330 | 430 | 145 | 50 | 955 |
| | XYL IV | 0.34 | 200 | 26 | <4 | <4 | <4 | 226 |
| Wheat arabinoxylan | XYL I | 1.12 | 24 | 120 | 115 | 31 | 4 | 294 |
| | XYL II | 1.40 | 18 | 300 | 110 | 9 | 4 | 441 |
| | XYL IV | 0.29 | 120 | 17 | <4 | <4 | <4 | 137 |

*Oligosaccharides are deacetylated during HPLC analysis, thus values represent both acetylated and non-acetylated xylo-oligosaccharides after hydrolysis.
+Total sum of Xyl + $Xyl_2$ + $Xyl_3$ + $Xyl_4$ + $Xyl_5$ Hex$^2$Xyl$_2$+Hex$^3$Xyl$_3$ for 1 h at 40° C. Almost complete hydrolysis of HexA$^3$Xyl$_3$ was obtained using 30 mg (500 nkat) of XYL-IV per gram of HexA$^3$Xyl$_3$ (Table 5, FIG. 4).

TABLE 5

Hydrolysis of HexA$^3$Xyl$_3$ by XYL-IV

| Dosage (mg/g) | Dosage (nkat/g) | HexAXyl$_3$ (mg/l) | HexAXyl$_2$ (mg/l) | Xyl (mg/l) | Xyl$_2$ (mg/l) |
|---|---|---|---|---|---|
| 0 | 0 | 270 | 115 | <4 | 7 |
| 0.65 | 10 | 260 | 130 | 6 | 9 |
| 3.2 | 51 | 220 | 160 | 18 | 7 |
| 6.5 | 104 | 150 | 190 | 30 | 8 |
| 32 | 512 | 13 | 270 | 30 | 8 |
| 65 | 1040 | <4 | 290 | 66 | 9 |
| 324 | 5200 | <4 | 290 | 67 | 8 |
| 648 | 10400 | <4 | 290 | 65 | 8 |

XYL-IV was effective for hydrolysis of several polymeric xylans from rye, unsubstituted xylan, MeGlcA-xylan, and arabinoxylan. Arabinoxylan was cleaved more slowly than the other two xylans, which were cleaved at approximately equal rates (FIG. 5).

Example 3

Substrate Hydrolysis by Combinations or Mixtures of XYLs-I, -II, and -IV

Hydrolysis of several substrates either simultaneously or sequentially with XYLs-I, -II, and -IV demonstrated that XYL-IV exhibits synergy with the other xylanases.

Table 6 and FIG. 6 show the results of a study in which a substrate was incubated individually with one of XYLs-I, -II, or -IV, or with a combination of these xylanases. The effect of added XYL-IV was more than additive. That is, synergy was observed. Although not limiting to the present invention, it is believed that this synergy is mainly due to XYL-IV's ability to hydrolyze linear and substituted oligosaccharides produced by XYL I and II.

TABLE 6

Synergy of XYL-IV With XYLs-I and -II

| Substrate | Enzyme | Dosage (nkat/g) | Reducing sugars (g/l) | Xyl (mg/l) | Xyl$_2$ (mg/l) | Xyl$_3$ (mg/l) | Xyl$_4$ (mg/l) | Xyl$_5$ (mg/l) | Tot* (mg/l) | Tot$_{xyl}$** (mg/l) |
|---|---|---|---|---|---|---|---|---|---|---|
| Unsubstituted xylan | XYL I | 100 | 0 | *** | | | | | | |
| | XYL II | 100 | 0 | | | | | | | |
| | XYL IV | 20 | 0.02 | | | | | | | |
| | XYL I + IV | 100 + 20 | 0.02 | | | | | | | |
| | XYL II + IV | 100 + 20 | 0.03 | | | | | | | |
| MeGlcA-xylan**** | XYL I | 100 | 0.23 | <4 | 6 | 13 | 12 | 14 | 45 | 49 |
| | XYL II | 100 | 0.14 | 6 | 4 | 11 | 10 | 10 | 41 | 38 |
| | XYL IV | 20 | 0.09 | 50 | 9 | <4 | <4 | <4 | 59 | 60 |
| | XYL I + IV | 100 + 20 | 0.66 | 420 | 69 | <4 | <4 | <4 | 489 | 493 |
| | XYL II + IV | 100 + 20 | 0.39 | 260 | 35 | <4 | <4 | <4 | 295 | 297 |
| Ac-MeGlcA-xylan***** | XYL I | 100 | 0.86 | 17 | 47 | 100 | 96 | 130 | 390 | 425 |
| | XYL II | 100 | 0.11 | <4 | 18 | 38 | 53 | 63 | 172 | 188 |
| | XYL IV | 20 | 0.58 | 16 | 16 | 5 | <4 | <4 | 37 | 39 |
| | XYL I + IV | 100 + 20 | 1.19 | 270 | 210 | 82 | 81 | 91 | 734 | 772 |
| | XYL II + IV | 100 + 20 | 0.90 | 190 | 110 | 67 | 47 | 72 | 486 | 512 |
| Rye arabinoxylan | XYL I | 100 | 0.76 | 4 | 20 | 21 | 14 | 7 | 66 | 71 |
| | XYL II | 100 | 0.81 | <4 | 45 | 25 | 10 | 5 | 85 | 92 |
| | XYL IV | 20 | 0.03 | 14 | <4 | <4 | <4 | <4 | 14 | 14 |
| | XYL I + IV | 100 + 20 | 0.98 | 175 | 19 | <4 | <4 | <4 | 194 | 195 |
| | XYL II + IV | 100 + 20 | 1.14 | 220 | 31 | 5 | <4 | <4 | 256 | 259 |

Conditions: pH 4, 40° C., 24 h, substrate concentration 5 g/l.
*Total sum of Xyl + Xyl$_2$ + Xyl$_3$ + Xyl$_4$ + Xyl$_5$.
**Total sum calculated as xylose.
***Not analyzed by HPLC.
****The degree of hydrolysis of this substrate was unusually low in these experiments.
*****Oligosaccharides are deacetylated during HPLC analysis, thus values represent both acetylated and non-acetylated xylo-oligosaccharides after hydrolysis.

Table 7 and FIG. 7 show the results of a study in which a substrate was incubated with XYL-I, this enzyme was heat inactivated, and then the substrate was incubated with XYL-IV. This resulted sequential cleavage of the substrate by XYL-I followed by XYL-IV. Once again, synergy was observed between XYL-I and XYL-IV.

TABLE 7

Stepwise Hydrolysis By XYL-I Followed by XYL-IV

| Substrate | Enzyme | XYL I Dosage (nkat/g) | Xyl (mg/l) | Xyl$_2$ (mg/l) | Xyl$_3$ (mg/l) | Xyl$_4$ (mg/l) | Xyl$_5$ (mg/l) | Tot* (mg/l) | Tot$_{xyl}$** (mg/l) |
|---|---|---|---|---|---|---|---|---|---|
| MeGlc-xylan | XYL I | 100 | 16 | 195 | 310 | 200 | 120 | 84 | 913 |
| | XYL I then XYL IV | 100 | 600 | 480 | <4 | <4 | <4 | 1080 | 1111 |
| | XYL I | 5000 | 360 | 1040 | 240 | 58 | 34 | 1732 | 1828 |
| | XYL I then XYL IV | 5000 | 750 | 1160 | <4 | <4 | <4 | 1910 | 1984 |
| Rye arabinoxylan | XYL I | 100 | <4 | 15 | 23 | 12 | 7 | 57 | 62 |
| | XYL I then XYL IV | 100 | 180 | 46 | <4 | <4 | <4 | 226 | 229 |
| | XYL I | 5000 | 45 | 64 | <4 | <4 | <4 | 109 | 113 |
| | XYL I then XYL IV | 5000 | 220 | 76 | <4 | <4 | <4 | 296 | 301 |

Conditions: pH 4, 40° C., 24 h + 24 h, substrate concentration 5 g/l;
XYL I (100 nkat/g or 5000 nkat/g) and XYL IV (20 nkat/g).
*Total sum of Xyl + XYL$_2$ + XYL$_3$ + XYL$_4$ + XYL$_5$.
**Total sum calculated as xylose.

Example 4

Preparation Of A Cloned DNA Molecule Encoding Trichoderma XYL-IV

The following is provided as a method of preparing a clone including an entire xyl4 gene described in Example 1. In this example, genomic DNA or cDNA clones derived from Trichoderma are prepared by using the following procedure. A pair of oligonucleotides suitable for use as PCR primers and based on the cDNA sequence of SEQ ID NO:1 are synthesized. Polymerase chain reaction (PCR) is performed using these primers and, as a template, total genomic DNA isolated from *Trichoderma reesei*, for example, strain QM6a (ATCC 13631). The DNA polymerase enzyme (e.g., Pwo polymerase), buffer and deoxynucleotide mixture used are supplied by Boehringer Mannheim. Typical conditions are used for PCR, such as; step 1, 1 min. at 94° C.; step 2, 40 sec. at 92° C.; step 3, 1 min. at 50° C., step 4, 2 min. at 72° C.; steps 2, 3 and 4 repeated 29 times; step 5, 5 min. at 72° C.

The major DNA product of PCR is digested with restriction enzymes, e.g., BglII and XbaI, recognizing sites added by the two primers and the resulting fragment is purified from an agarose electrophoresis gel. This DNA fragment is ligated with an appropriate vector that has been digested with the same restriction enzymes, for example, pSL1180 (Pharmacia) which had been digested with, e.g., BglII and XbaI. The resulting plasmid is typically sequenced to confirm that the insert corresponds to the expected fragment of the Trichoderma xyl4 gene. The DNA sequence reveals the presence of any introns and exons in the gene.

The plasmid, or the insert it contains, can now be used as a hybridization probe to allow the entire xyl4 gene to be cloned from any genomic DNA or cDNA libraries of interest. Because there are not CBD or linker (hinge) regions, the XYL-IV encoding DNA within the plasmid does not include these regions. Therefore, by design, it would be expected to hybridize with other xyl4 DNA sequences but not to CBD encoding sequences which may be part of other xylanase or glycosidase genes.

Total genomic DNA from *T. reesei*, for example, strain QM6a, is digested separately with a variety of different restriction endonucleases and subjected to agarose gel electrophoresis. The DNA was subsequently blotted to a Nytran (S&S) membrane filter and probed with suitable xyl4 DNA fragment isolated from the plasmid and labeled with $^{32}$P by the Megaprime random labeling system supplied by Amersham. Hybridization with the probe was performed at moderate stringency in a typical buffer, for example, containing 30% formamide, 5×SSPE, 0.5% SDS at 38° C. The membrane filter was subsequently washed at moderate stringency, for example, in 2×SSC, 0.1% SDS at 55° C. before being exposed to X-ray film. The results indicate that the genomic copy of the *T. reesei* xyl4 gene resides on an appropriate restriction fragment.

Given the exemplified xyl4 gene as provided above, it would be routine for one of skill in the art to clone the *Trichoderma reesei* xyl4 gene from genomic DNA or cDNA libraries by colony hybridization using a PCR fragment inserted in a plasmid as described above as a probe.

Example 5

Method of Isolating DNA Sequences Encoding XYL-IVs In Microorganisms

The general technique in Examples 1 and 4 may be adapted in conjunction with known techniques to obtain clones including XYL-IV genes from other fungi and bacteria. A suitable plasmid or an isolated DNA insert encoding part of the xyl4 gene may be labeled as can the whole molecule of the xyl4. This DNA probe can then be used to hybridize with genomic DNA or cDNA from other fungi or bacteria. A comparison of the deduced amino acid sequence of the Trichoderma XYL-IV with the known amino acid sequences of other xylanases identifies certain regions of amino acids that are conserved between XYL-IV and other xylanases. These conserved regions provide the basis for designing degenerate primers for use in PCR amplification of XYL-IV-encoding DNA from other microorganisms. Such methods are generally known in the art and considered routine (see e.g., McPherson, et al., *PCR A PRACTICAL*

*APPROACH* pp. 171–186 (1991)). The oligonucleotides derived from one or more of these amino acid sequences would be used as primers for routine PCR experiments using genomic DNA. Genomic DNA or cDNA could then easily be obtained from any microorganism and used as a template in such PCR experiments. In this way it would be possible to clone genes encoding a XYL-IV from a variety of microorganisms.

Example 6

Heterologous Hybridization Method for Isolating XYL-IV Encoding Sequences from Other Microorganisms Genomic DNA from different microorganisms can be digested with an appropriate restriction enzyme, such as HindIII, and run on a 1.0% agarose gel. The gel is depurinated, denatured and blotted, and the membrane is UV-crosslinked by known procedures. Prehybridization, hybridization, labeling of the probe and detection are done using known methods, such as the DIG/Genius™ System from Boehringer Mannheim.

A probe corresponds to the nucleotide sequence encoding the whole molecule of *T. reesei* XYL-IV. The original cDNA subclone (EXAMPLE 1) is digested with an appropriate pair of restriction enzymes and the resulting fragment is labeled with DIG-dUTP (digoxigenin-dUTP) via random-primed labeling according to manufacturer's (Boehringer Mannheim) instructions.

The membrane is prehybridized and then hybridized in an appropriate blocking reagent, such as 5×SSC-0.1% N-lauroylsarcosine-0.02% SDS-1% Genius™ blocking reagent, at a suitable temperature, such as 45 ° C. Hybridization (typically over night) is followed by washes. Then detection with an appropriate conjugate and visualization, such as with a chemiluminescence substrate CSPD®, are done according to manufacturer's instructions.

This method and variations of it (different hybridization and washing conditions) can be used to detect XYL-IV encoding genes from any organism.

The invention has been described with reference to various specific and preferred embodiments and techniques. However, it should be understood that many variations and modifications may be made while remaining within the spirit and scope of the invention.

We claim:

1. An isolated xylanase (XYL-IV) comprising the amino acid sequence of SEQ ID NO: 2.

2. The isolated XYL-IV of claim 1, wherein the XYL-IV is derived from a filamentous fungus.

3. The isolated XYL-IV of claim 2, wherein the filamentous fungus is a Trichoderma spp.

4. A method of altering the properties of a xylan containing substrate comprising
   (a) obtaining a host cell which has been transformed with a vector comprising DNA encoding a xylanase (XYL-IV) having the amino acid sequence of SEQ ID NO: 2;
   (b) culturing the host cell under conditions suitable for the expression of the XYL-IV;
   (c) recovering the XYL-IV; and
   (d) contacting the xylan containing substrate with a composition including the XYL-IV.

5. The method according to claim 4, wherein the host cell is a filamentous fungal cell.

6. The method according to claim 4, wherein the host cell is from a strain of Bacillus or a strain of *Escherichia coli*.

7. The method of claim 4, wherein said method comprises altering the handling properties of animal feed and food products.

8. The method of claim 4, wherein said method comprises altering plant materials.

9. The method of claim 4, wherein said method comprises altering the properties of wood pulp or derivatives thereof during the manufacture of paper.

10. The method of claim 4, wherein said method comprises altering the properties of xylan containing biomass during its reduction to glucose.

* * * * *